US012674148B2

(12) United States Patent
Kwon et al.

(10) Patent No.: US 12,674,148 B2
(45) Date of Patent: Jul. 7, 2026

---

(54) CELL-BASED REPORTER ASSAY FOR SCREENING INHIBITORS OF CORONAVIRUS RNA-DEPENDENT RNA POLYMERASE ACTIVITY

(71) Applicant: KOREA INSTITUTE OF ORIENTAL MEDICINE, Daejeon (KR)

(72) Inventors: Sun Oh Kwon, Daejeon (KR); Young Hee Jin, Daejeon (KR); Jung Sun Min, Daejeon (KR)

(73) Assignee: KOREA INSTITUTE OF ORIENTAL MEDICINE, Daejeon (KR)

( * ) Notice: Subject to any disclaimer, the term of this patent is extended or adjusted under 35 U.S.C. 154(b) by 959 days.

(21) Appl. No.: 17/778,197

(22) PCT Filed: Sep. 29, 2020

(86) PCT No.: PCT/KR2020/013330
§ 371 (c)(1),
(2) Date: May 19, 2022

(87) PCT Pub. No.: WO2021/149893
PCT Pub. Date: Jul. 29, 2021

(65) Prior Publication Data
US 2023/0242901 A1     Aug. 3, 2023

(30) Foreign Application Priority Data
Jan. 22, 2020    (KR) ........................ 10-2020-0008687

(51) Int. Cl.
*C12N 9/12*        (2006.01)
*A61P 31/14*       (2006.01)
(Continued)

(52) U.S. Cl.
CPC .............. *C12N 9/127* (2013.01); *A61P 31/14* (2018.01); *C12N 15/1055* (2013.01); *C12Q 1/66* (2013.01);
(Continued)

(58) Field of Classification Search
CPC ......... C12N 9/127; C12N 2770/20011; C12Q 1/66; A61P 31/14
See application file for complete search history.

(56) References Cited

U.S. PATENT DOCUMENTS

2006/0039926 A1    2/2006   Denison
2008/0241922 A1    10/2008  Wu et al.
2019/0030187 A1    1/2019   Lu et al.

FOREIGN PATENT DOCUMENTS

CN      1718731 A    1/2006
EP      3196308 A1   7/2017
(Continued)

OTHER PUBLICATIONS

Pan, J., et al., Oct. 2008, Genome-Wide Analysis of Protein-Protein Interactions and Involvement of Viral Proteins in SARS-COV Replication, PLoS One, 3(10):e3299, pp. 1-11.*
(Continued)

*Primary Examiner* — Jeffrey S Parkin
(74) *Attorney, Agent, or Firm* — Meunier Carlin & Curfman LLC

(57) ABSTRACT

The present invention relates to a screening composition for a therapeutic agent for coronavirus infection, comprising a CoV RdRp expression vector and a bicistronic reporter vector, a screening kit for a therapeutic agent for coronavirus infection, comprising the composition, and a method for screening a therapeutic agent for coronavirus infection using the composition or kit. When the screening composition for a therapeutic agent for coronavirus infection, provided by
(Continued)

the present invention, is used, candidate materials that can have direct influences on the activity of CoV RdRp can be screened more quickly and easily, and thus, the composition can be widely used in the development of therapeutic agents for coronavirus infection.

22 Claims, 14 Drawing Sheets

Specification includes a Sequence Listing.

(51) Int. Cl.

| *C12N 15/10* | (2006.01) |
|---|---|
| *C12Q 1/66* | (2006.01) |
| *C12N 15/85* | (2006.01) |

(52) U.S. Cl.
CPC .... *C12N 15/85* (2013.01); *C12N 2770/20011* (2013.01)

(56) References Cited

FOREIGN PATENT DOCUMENTS

| KR | 1020110013467 A | 2/2011 |
|---|---|---|
| KR | 101274008 B1 | 6/2013 |
| KR | 20160138943 A | 12/2016 |
| KR | 1020170051884 A | 5/2017 |
| KR | 20020010241 A | 2/2022 |
| WO | 2017078421 A1 | 5/2017 |

OTHER PUBLICATIONS

Lee, J.-C., et al., 2010, A cell-based reporter assay for inhibitor screening of hepatitis C virus RNA-dependent RNA polymerase, Anal. Biochem. 403:52-62.*

Cotten, M., et al., Jan./Feb. 2014, Spread, circulation, and evolution of the Middle East respiratory syndrome virus, mBio 5(1):e01062-13, pp. 1-11.*

UniProtKB R9UPC1_MERS sequence listing, submitted Sep. 2013, referenced by Cotten et al., 2014, mBio, 5(1):e01062-13, pp. 1-11.*

Cevik, B., 2013, The RNA-dependent RNA polymerase of Citrus tristeza virus forms oligomers, Virol. 447:121-130.*

Subissi, L., et al., Sep. 2014, One severe acute respiratory syndrome coronavirus protein complex integrates processive RNA polymerase and exonuclease activities, PNAS, E3900-E3909.*

Wu, F., et al., Mar. 2020, A new coronavirus associated with human respiratory disease in China, Nature 579:265-271.*

Wu, F., et al., Mar. 2020, Sever acute respiratory syndrome coronavirus 2 isolate Wuhan-Hu-1, complete genome, GenBank MN908947.3.*

Germain-Genevois, C., et al., 2016, Detection of brain tumors and systemic metastases using NanoLuc and Fluc for dual reporter imaging, Mol. Imaging Biol. 18:62-69.*

Notice of Allowance issued in Korean Application No. 2022-039453307, mailed May 27, 2022, 4 pages.

Extended European Search report issued for Application No. EP20915752.8, dated Feb. 7, 2024.

Terada, Y., et al. "Establishment of a Virulent Full-Length cDNA Clone for Type I Feline Coronavirus Strain C3663." Journal of Virology. Nov. 2019, vol. 93, Issue 21, e01208-19, inner pp. 1-17.

Kirchdoerfer, R.N., et al. "Structure of the SARS-COV nsp12 polymerase bound to nsp 7 and nsp 8 co-factors." May 28, 2019. Nature Communications. vol. 10, No. 2342, inner pp. 1-9.

Sakai, Y., et al. "Two-amino acids change in the nsp4 of SARS coronavirus abolishes viral replication." Jul. 21, 2017. Virology. vol. 510, pp. 165-174.

English Translation of International Search Report in Application No. PCT/KR2020/013330, mailed Jan. 18, 2021, 3 pages.

* cited by examiner

[Fig. 1]

5'— ▶ | FLuc | - | Rbz | ᴚTU-ʹƐ | ɔn˥N | ᴚTU-ʹϚ | Rbz | - 3'

↓ Transcription mRNA | FLuc |  | Rbz | ᴚTU-ʹƐ | ɔn˥N | ᴚTU-ʹϚ | Rbz |

↓ Translation                    ↓ Ribozyme cis-cleavage (FLuc)

5'— | ᴚTU-ʹƐ | ɔn˥N | ᴚTU-ʹϚ | — 3' (-)RNA

⇅ RNA-dependent RNA polymerase

5'— | 5'-UTR | NLuc | 3'-UTR | — 3' (+)RNA

↓ Translation (NLuc)

▶ CoV nsp expression vector

5'— ▶ | CoV nsp12 | - 3'
5'— ▶ | CoV nsp 8 | - 3'     ⟶     (RdRp)
5'— ▶ | CoV nsp 7 | - 3'    Transcription & Translation

[Fig. 2a]

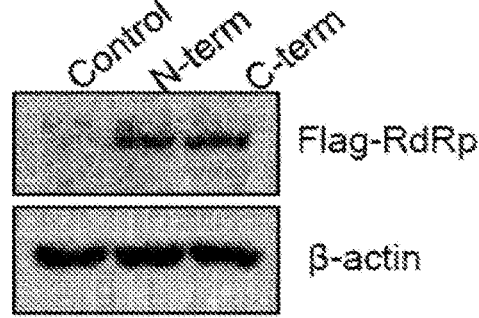

Control  N-term  C-term

Flag-RdRp

β-actin

[Fig. 2b]
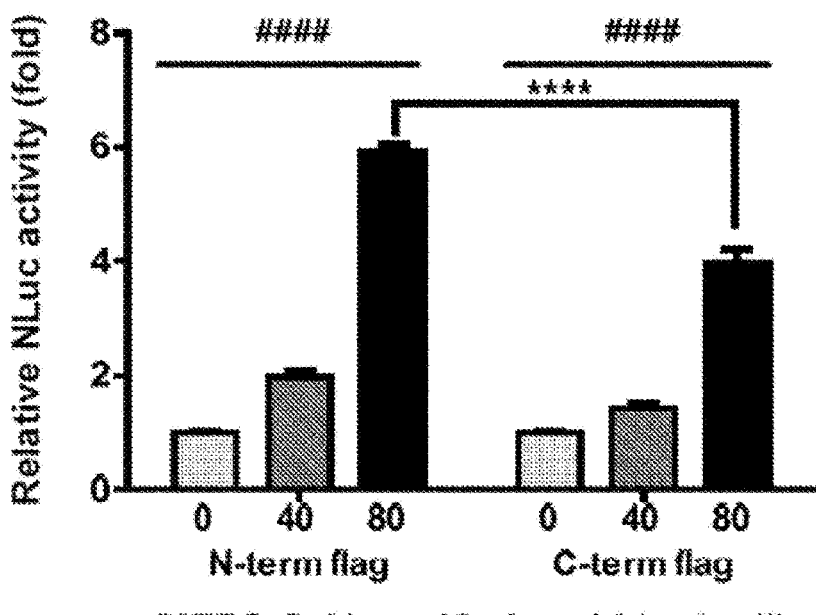
[Fig. 2c]
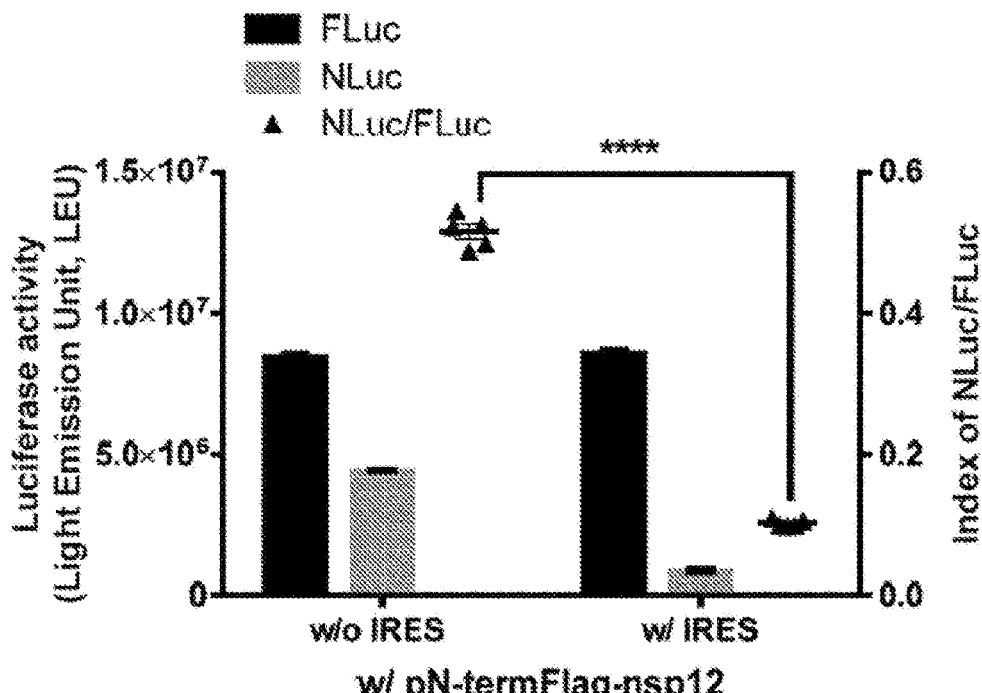

[Fig. 2d]
nsp7-C-Flag   +   -
nsp8-C-Flag   +   -
nsp12-N-Flag   +   -
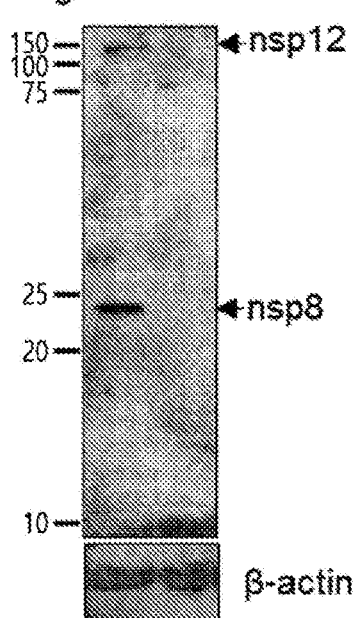
[Fig. 2e]
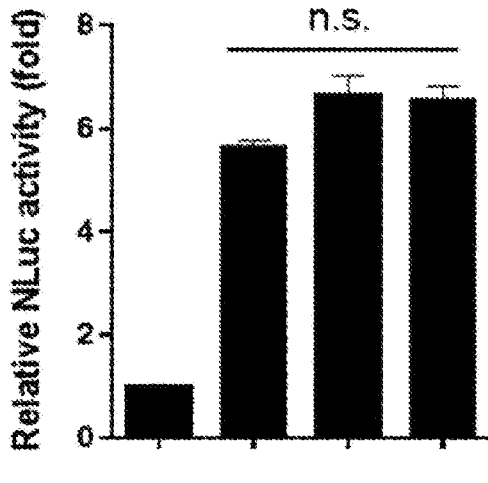

[Fig. 3a]
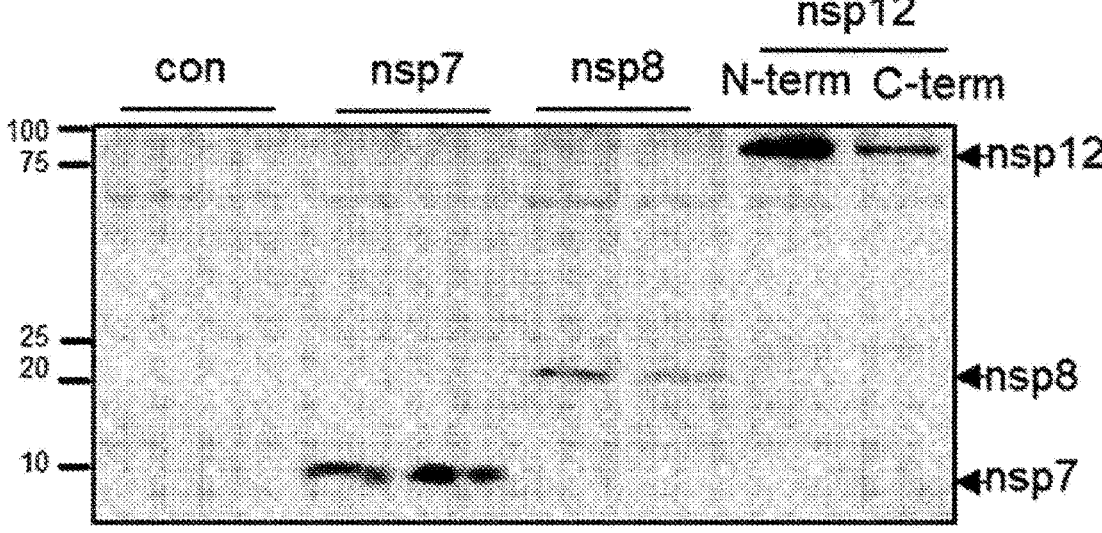
[Fig. 3b]
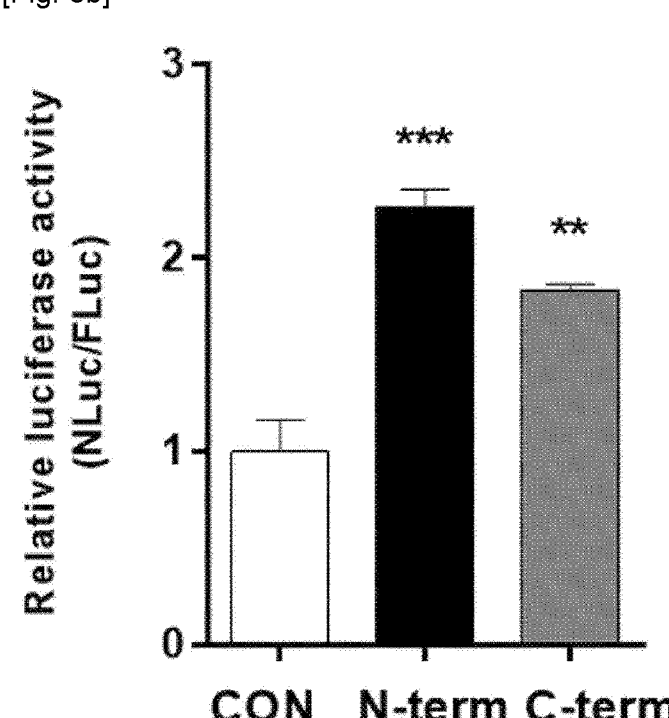

[Fig. 3c]
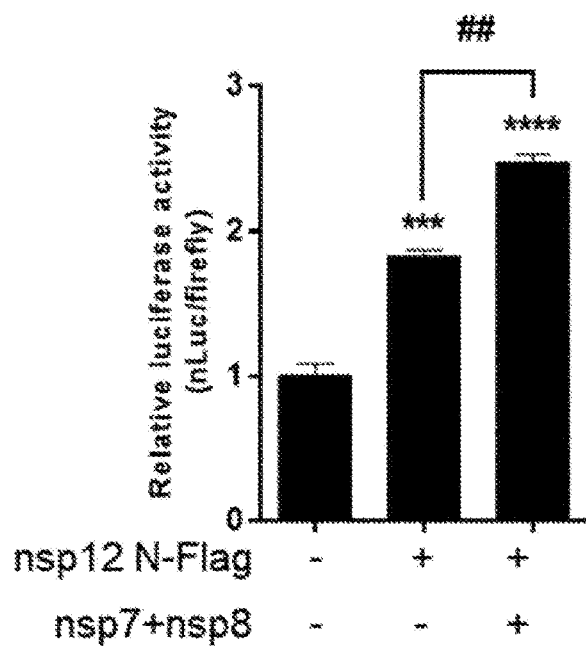
[Fig. 3d]
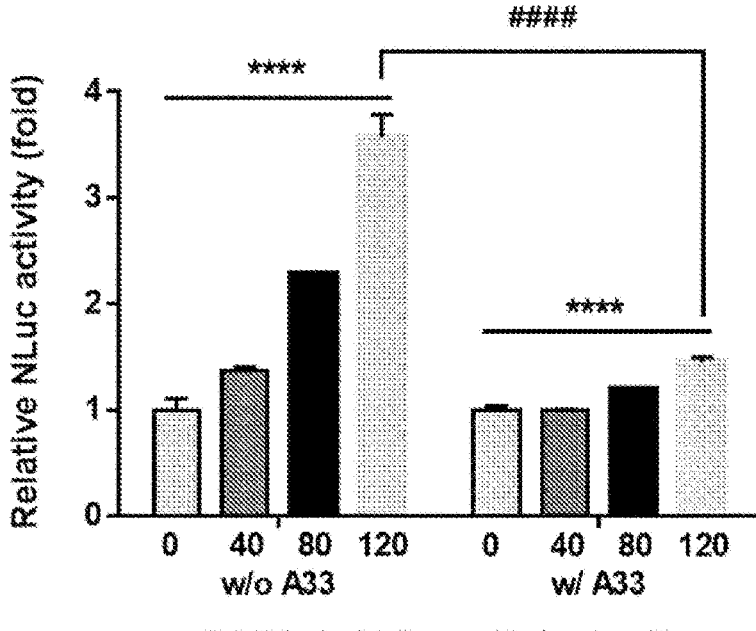

[Fig. 4a]
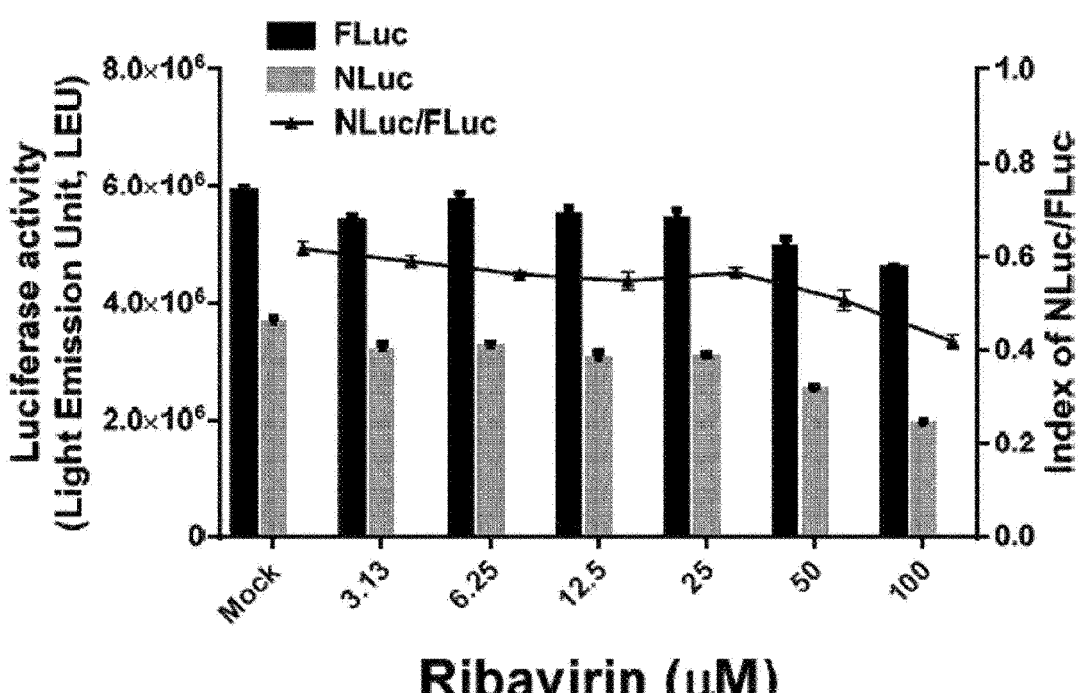
Ribavirin (µM)
[Fig. 4b]
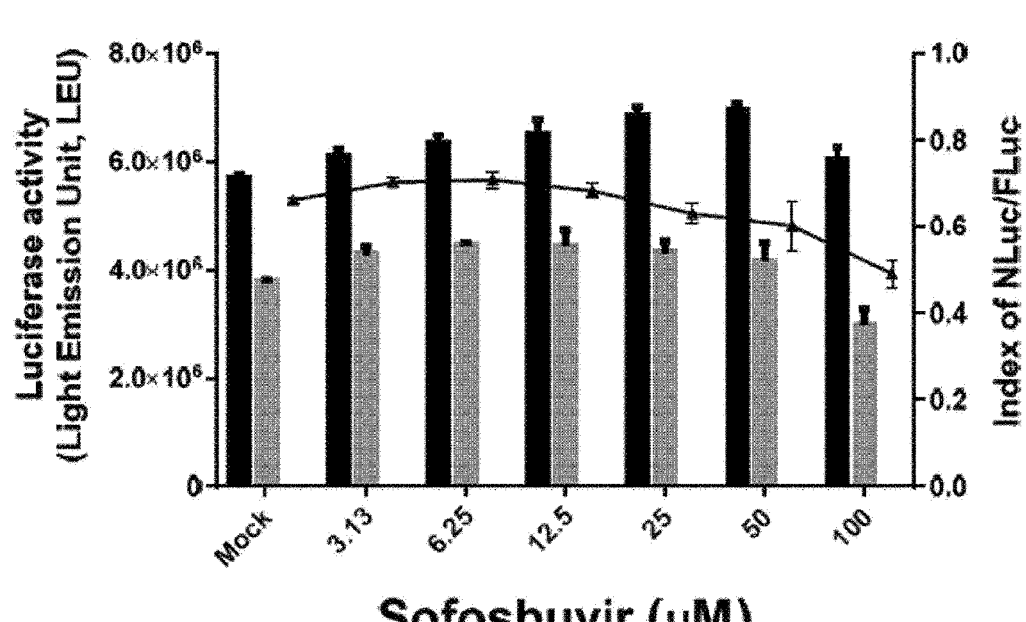
Sofosbuvir (µM)

[Fig. 4c]
[Fig. 4d]
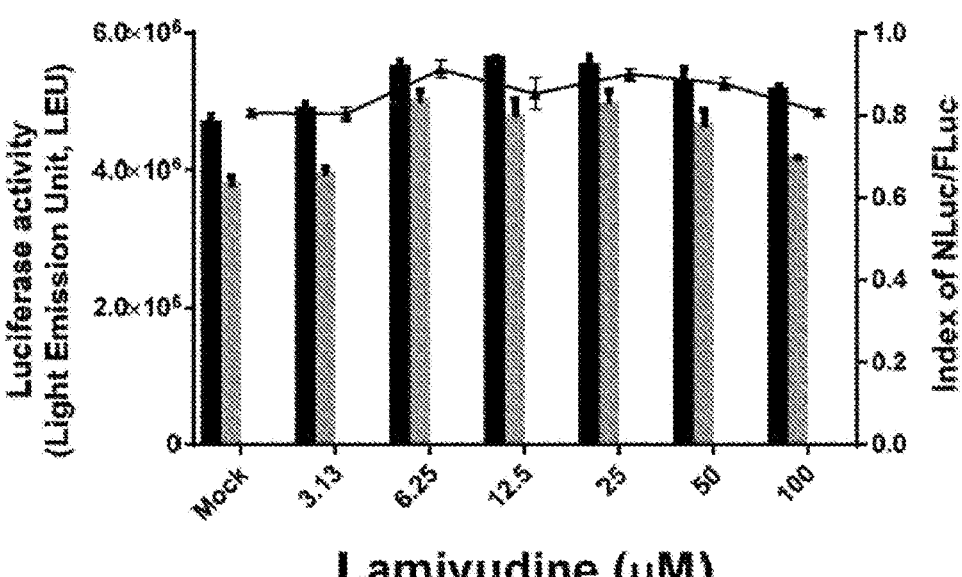

[Fig. 4e]
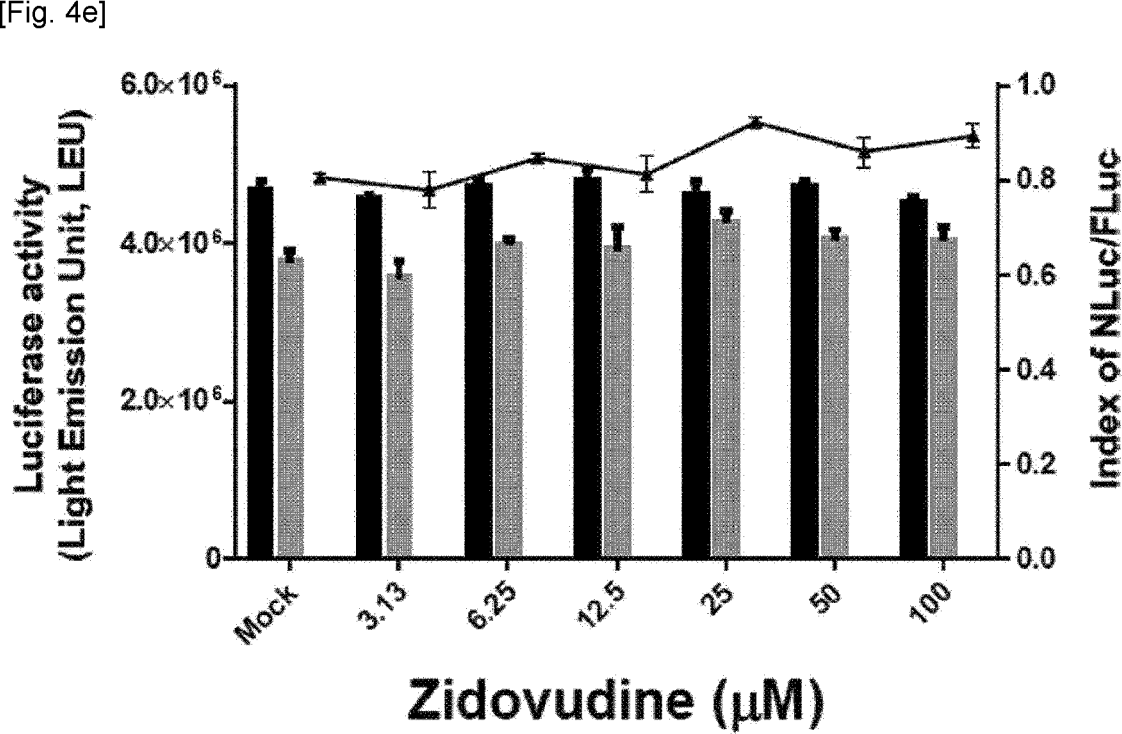
Zidovudine (μM)
[Fig. 4f]
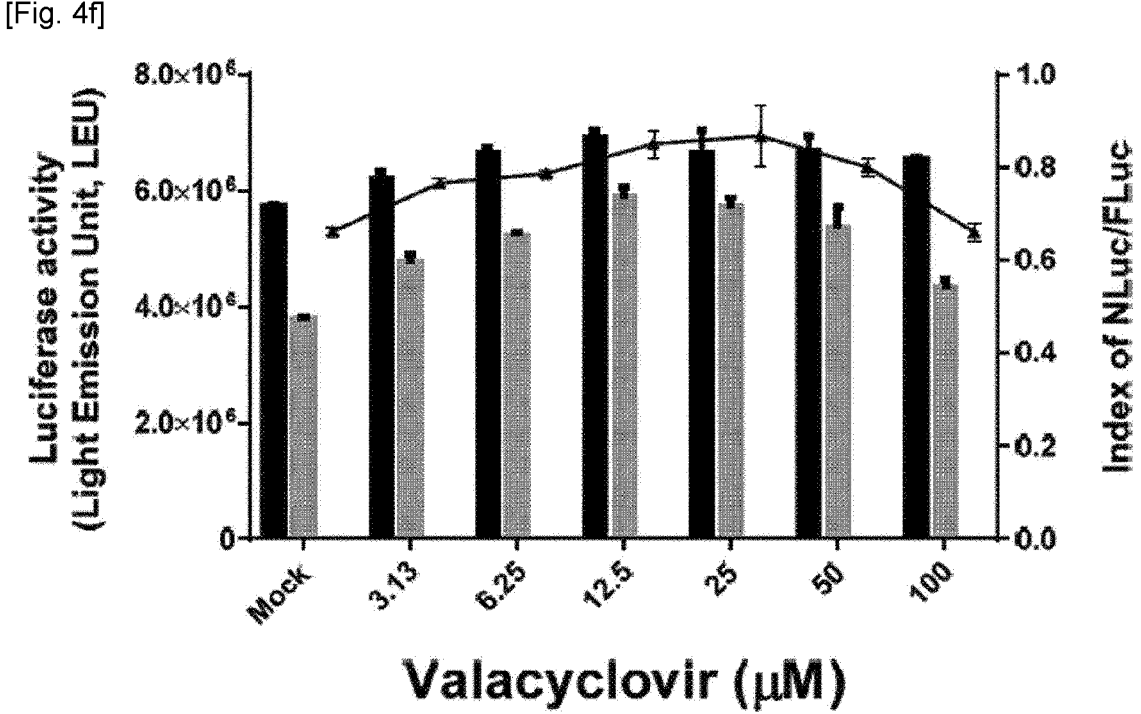
Valacyclovir (μM)

[Fig. 4g]
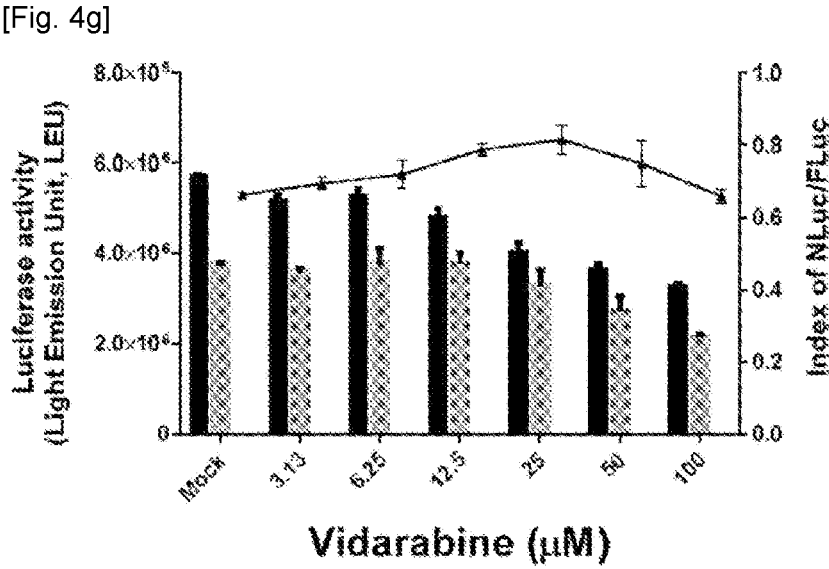
[Fig. 5a]
[Fig. 5b]

[Fig. 5c]
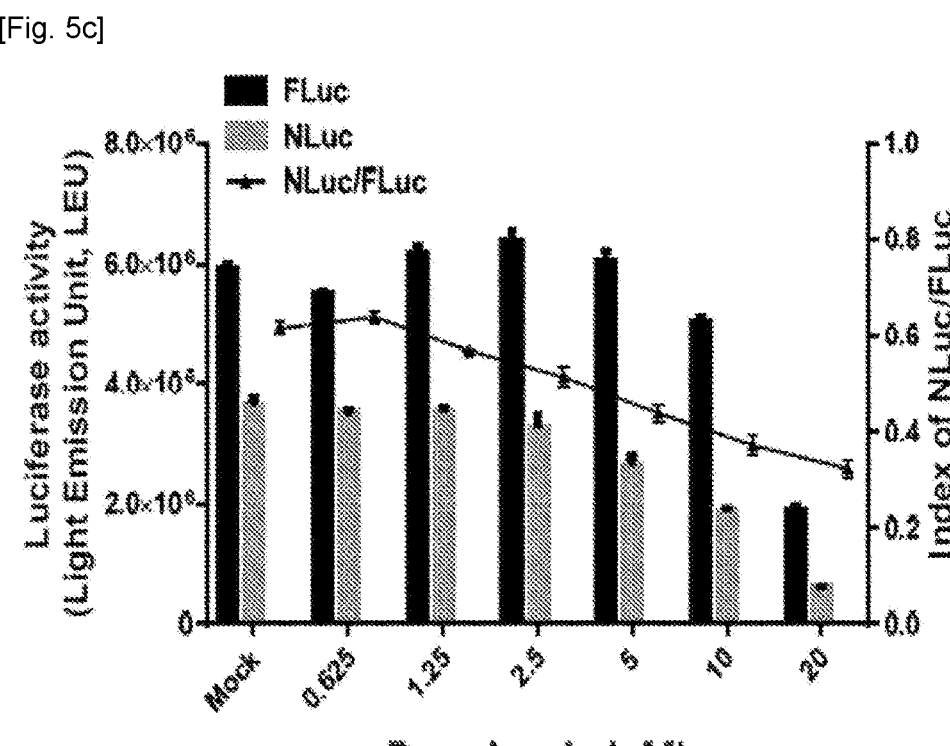
[Fig. 5d]
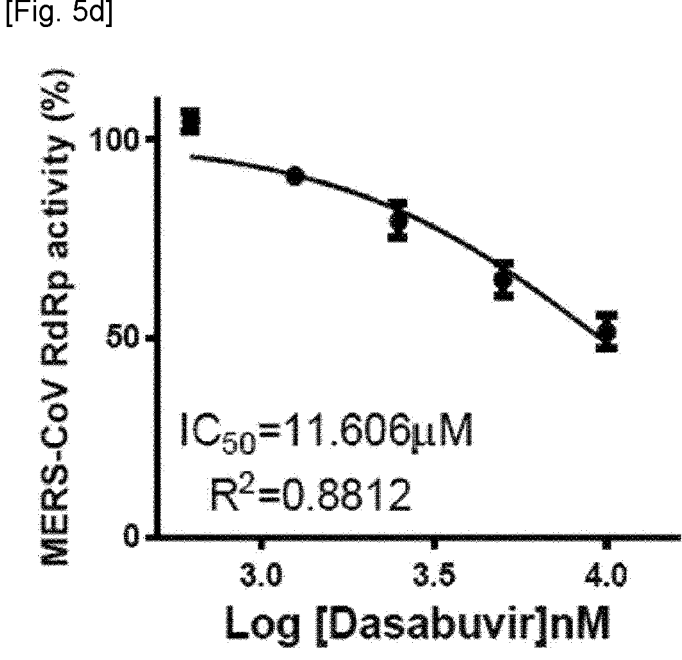

[Fig. 6a]
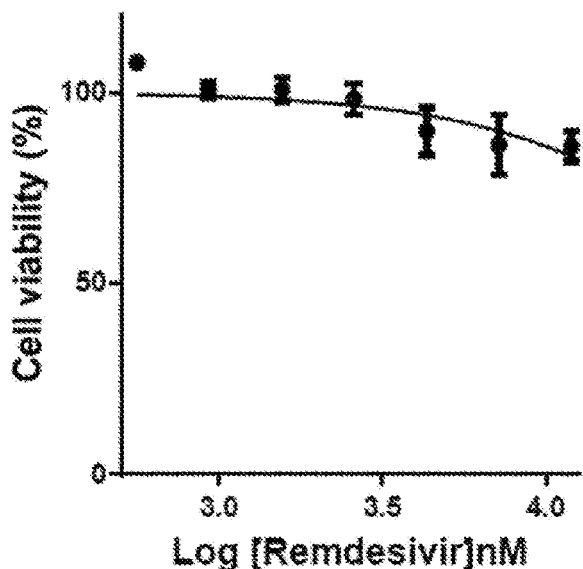
[Fig. 6b]

[Fig. 6c]
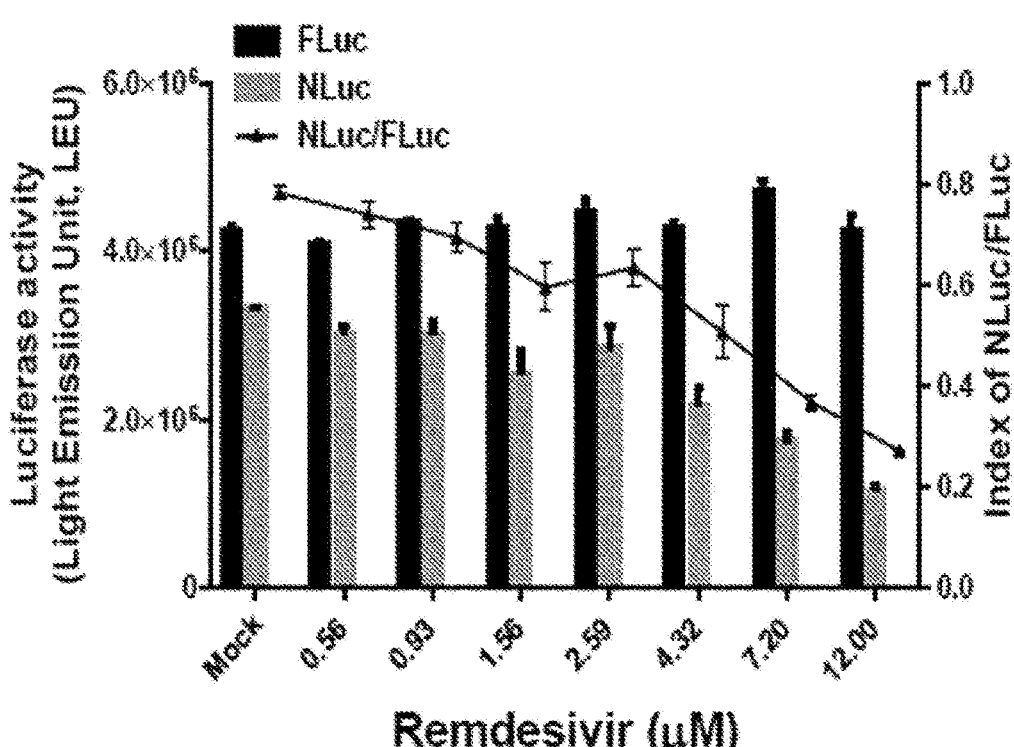
[Fig. 6d]
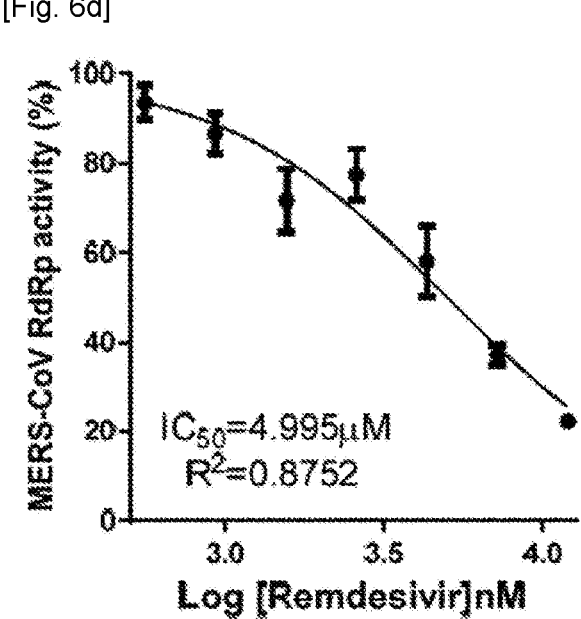

[Fig. 7a]
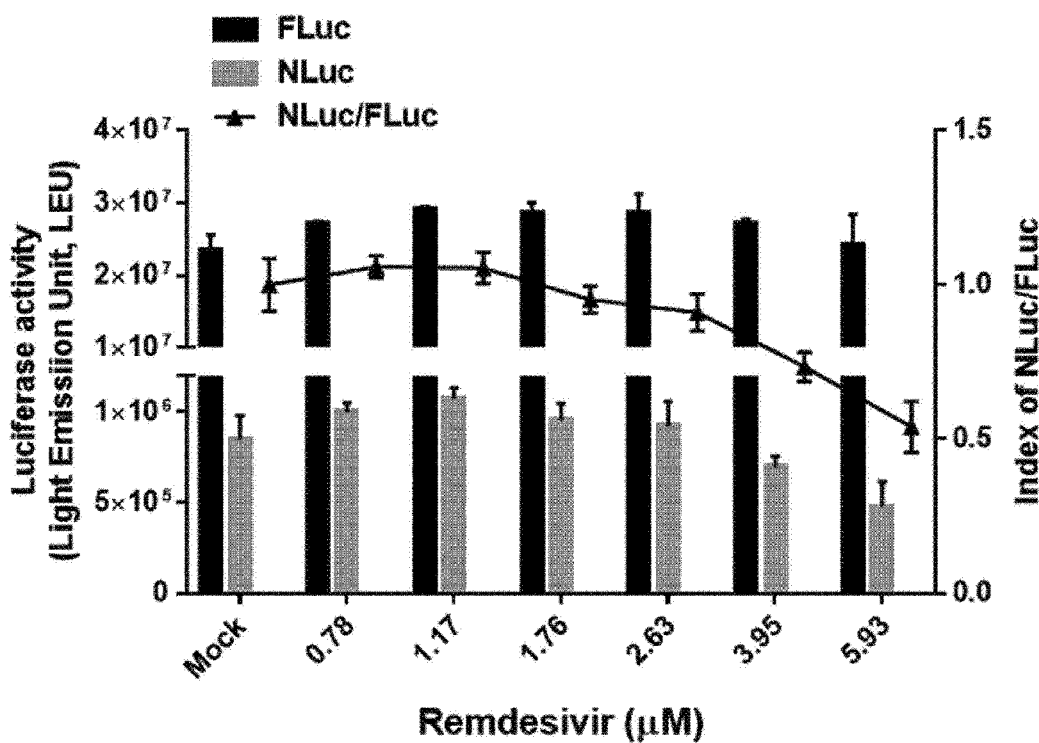
[Fig. 7b]
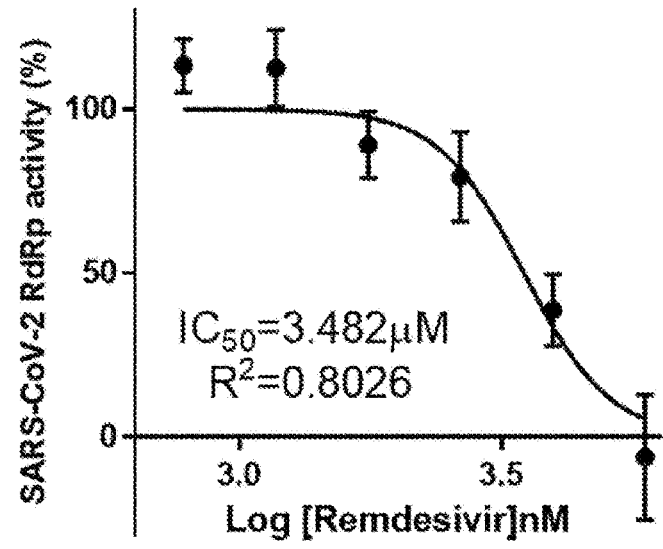

[Fig. 8]
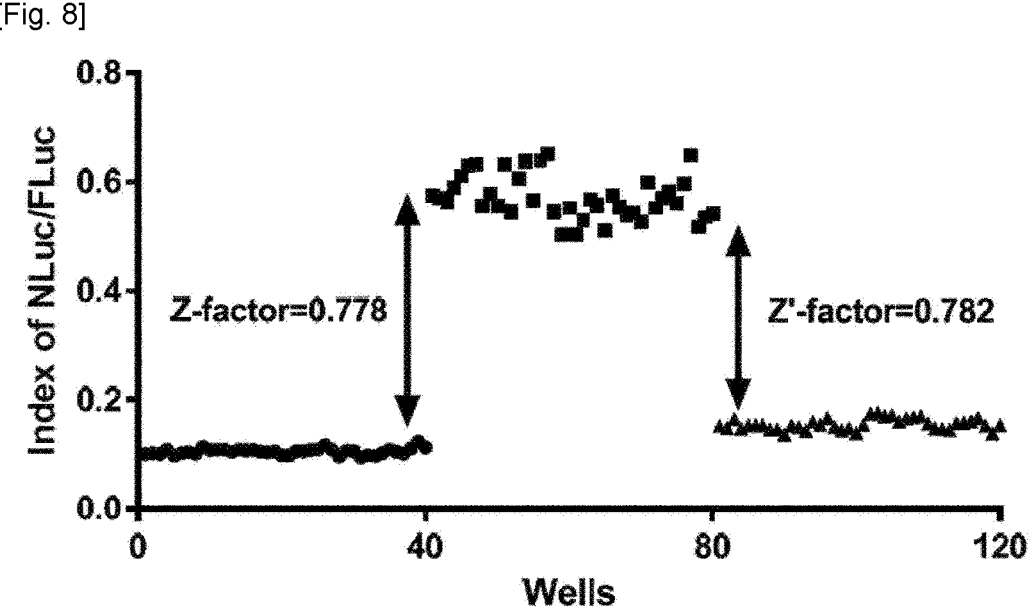
● Negative : pcDNA3.1 + 0.025% DMSO
■ Positive : pN-termFlag-nsp12 + 0.025% DMSO
▲ Inhibitor : pN-termFlag-nsp12 + 12 μM Remdesivir

SEQUENCE LISTING

<160> NUMBER OF SEQ ID NOS: 8

<210> SEQ ID NO 1
<211> LENGTH: 2798
<212> TYPE: DNA
<213> ORGANISM: Artificial Sequence
<220> FEATURE:
<223> OTHER INFORMATION: Synthetic Construct

<400> SEQUENCE: 1

-continued

```
tctaaagatt ccaatttttt aaacgagtcc ggggttctat tgtaaatgcc cgaatagaac      60
cctgttcaag tggtttgtcc actgatgtcg tctttagggc atttgacatc tgcaactata     120
aggctaaggt tgctggtatt ggaaaatact acaagactaa tacttgtagg tttgtagaat     180
tagatgacca agggcatcat ttagactcct attttgtcgt taagaggcat actatggaga     240
attatgaact agagaagcac tgttacgatt tgttacgtga ctgtgatgct gtagctcccc     300
atgatttctt catctttgat gtagacaaag ttaaaacacc tcatattgta cgtcagcgtt     360
taactgagta cactatgatg gatcttgtat atgccctgag gcactttgat caaaatagcg     420
aagtgcttaa ggctatctta gtgaagtatg gttgctgtga tgttacctac tttgaaaata     480
aactctggtt tgattttgtt gaaaatccca gtgttattgg tgtttatcat aaacttggag     540
aacgtgtacg ccaagctatc ttaaacactg ttaaattttg tgaccacatg gtcaaggctg     600
gtttagtcgg tgtgctcaca ctagacaacc aggaccttaa tggcaagtgg tatgattttg     660
gtgacttcgt aatcactcaa cctggttcag gagtagctat agttgatagc tactattctt     720
atttgatgcc tgtgctctca atgaccgatt gtctggccgc tgagacacat agggattgtg     780
attttaataa accactcatt gagtggccac ttactgagta tgattttact gattataagg     840
tacaactctt tgagaagtac tttaaatatt gggatcagac gtatcacgca aattgcgtta     900
attgtactga tgaccgttgt gtgttacatt gtgctaattt caatgtattg tttgctatga     960
ccatgcctaa gacttgtttc ggacccatag tccgaaagat ctttgttgat ggcgtgccat    1020
ttgtagtatc ttgtggttat cactacaaag aattaggttt agtcatgaat atggatgtta    1080
gtctccatag acataggctc tctcttaagg agttgatgat gtatgccgct gatccagcca    1140
tgcacattgc ctcctctaac gctttcttg atttgaggac atcatgtttt agtgtcgctg    1200
cacttacaac tggtttgact tttcaaactg tgcggcctgg caattttaac caagacttct    1260
atgatttcgt ggtatctaaa ggtttcttta aggagggctc ttcagttacg ctcaaacatt    1320
ttttctttgc tcaagatggt aatgctgcta ttacagatta taattactat tcttataatc    1380
tgcctactat gtgtgacatc aaacaaatgt tgttctgcat ggaagttgta aacaagtact    1440
tcgaaatcta tgacggtggt tgtcttaatg cttctgaagt ggttgttaat aatttagaca    1500
agagtgctgg ccatccttt aataagtttg gcaaagctcg tgtctattat gagagcatgt    1560
cttaccagga gcaagatgaa ctctttgcca tgacaaagcg taacgtcatt cctaccatga    1620
ctcaaatgaa tctaaaatat gctattagtg ctaagaatag agctcgcact gttgcaggcg    1680
tgtccatact tagcacaatg actaatcgcc agtaccatca gaaaatgctt aagtccatgg    1740
ctgcaactcg tggagcgact tgcgtcattg gtactacaaa gttctatggt ggctgggatt    1800
tcatgcttaa aacattgtac aaagatgttg ataatccgca tcttatgggt tgggattacc    1860
ctaagtgtga tagagctatg cctaatatgt gtagaatctt cgcttcactc atattagctc    1920
gtaaacatgg cacttgttgt gtactacaaggg acagatttta tcgcttggca aatgagtgtg    1980
ctcaggtgct aagcgaatat gttctatgtg gtggtggtta ctacgtcaaa cctggaggta    2040
ccagtagcgg agatgccacc actgcatatg ccaatagtgt ctttaacatt ttgcaggcga    2100
caactgctaa tgtcagtgca cttatgggtg ctaatggcaa caagattgtt gacaaagaag    2160
ttaaagacat gcagtttgat ttgtatgtca atgtttacag gagcactagc ccagacccca    2220
aatttgttga taaatactat gctttttctta ataagcactt ttctatgatg atactgtctg    2280
atgacggtgt cgtttgctat aatagtgatt atgcagctaa gggttacatt gctggaatac    2340
```

-continued

```
agaattttaa ggaaacgctg tattatcaga acaatgtctt tatgtctgaa gctaaatgct    2400
gggtggaaac cgatctgaag aaagggccac atgaattctg ttcacagcat acgctttata    2460
ttaaggatgg cgacgatggt tacttccttc cttatccaga cccttcaaga attttgtctg    2520
ccggttgctt tgtagatgat atcgttaaga ctgacggtac actcatggta gagcggtttg    2580
tgtctttggc tatagatgct taccctctca caaagcatga agatatagaa taccagaatg    2640
tattctgggt ctacttacag tatatagaaa aactgtataa agaccttaca ggacacatgc    2700
ttgacagtta ttctgtcatg ctatgtggtg ataattctgc taagttttgg gaagaggcat    2760
tctacagaga tctctatagt tcgcctacca ctttgcag                            2798
```

<210> SEQ ID NO 2
<211> LENGTH: 2796
<212> TYPE: DNA
<213> ORGANISM: Artificial Sequence
<220> FEATURE:
<223> OTHER INFORMATION: Synthetic Construct

<400> SEQUENCE: 2

```
tcagctgatg cacaatcgtt tttaaacggg tttgcggtgt aagtgcagcc cgtcttacac      60
cgtgcggcac aggcactagt actgatgtcg tatacagggc ttttgacatc tacaatgata     120
aagtagctgg ttttgctaaa ttcctaaaaa ctaattgttg tcgcttccaa gaaaaggacg     180
aagatgacaa tttaattgat tcttactttg tagttaagag acacactttc tctaactacc     240
aacatgaaga aacaatttat aatttactta aggattgtcc agctgttgct aaacatgact     300
tctttaagtt tagaatagac ggtgacatgg taccacatat atcacgtcaa cgtcttacta     360
aatacacaat ggcagacctc gtctatgctt taaggcattt tgatgaaggt aattgtgaca     420
cattaaaaga aatacttgtc acatacaatt gttgtgatga tgattatttc aataaaaagg     480
actggtatga ttttgtagaa aacccagata tattacgcgt atacgccaac ttaggtgaac     540
gtgtacgcca agctttgtta aaaacagtac aattctgtga tgccatgcga aatgctggta     600
ttgttggtgt actgacatta gataatcaag atctcaatgg taactggtat gatttcggtg     660
atttcataca aaccacgcca ggtagtggag ttcctgttgt agattcttat tattcattgt     720
taatgcctat attaaccttg accagggctt taactgcaga gtcacatgtt gacactgact     780
taacaaagcc ttacattaag tgggatttgt taaaatatga cttcacggaa gagaggttaa     840
aactctttga ccgttatttt aaatattggg atcagacata ccacccaaat tgtgttaact     900
gtttggatga cagatgcatt ctgcattgtg caaactttaa tgttttattc tctacagtgt     960
tcccacctac aagtttttgga ccactagtga gaaaaatatt tgttgatggt gttccatttg    1020
tagtttcaac tggataccac ttcagagagc taggtgttgt acataatcag gatgtaaact    1080
tacatagctc tagacttagt tttaaggaat tacttgtgta tgctgctgac cctgctatgc    1140
acgctgcttc tggtaatcta ttactagata aacgcactac gtgctttttca gtagctgcac    1200 ttactaacaa tgttgctttt caaactgtca aacccggtaa ttttaacaaa gacttctatg    1260
actttgctgt gtctaagggt ttcttttaagg aaggaagttc tgttgaatta aaacacttct    1320
tctttgctca ggatggtaat gctgctatca gcgattatga ctactatcgt tataatctac    1380
caacaatgtg tgatatcaga caactactat ttgtagttga agttgttgat aagtactttg    1440
attgttacga tggtggctgt attaatgcta ccaagtcat cgtcaacaac ctagacaaat    1500
cagctggttt tccatttaat aaatgggggta aggctagact ttattatgat tcaatgagtt    1560
atgaggatca agatgcactt ttcgcatata caaaacgtaa tgtcatccct actataactc    1620
```

```
aaatgaatct taagtatgcc attagtgcaa agaatagagc tcgcaccgta gctggtgtct    1680
ctatctgtag tactatgacc aatagacagt ttcatcaaaa attattgaaa tcaatagccg    1740
ccactagagg agctactgta gtaattggaa caagcaaatt ctatggtggt tggcacaaca    1800
tgttaaaaac tgtttatagt gatgtagaaa accctcacct tatgggttgg gattatccta    1860
aatgtgatag agccatgcct aacatgctta gaattatggc ctcacttgtt cttgctcgca    1920
aacatacaac gtgttgtagc ttgtcacacc gtttctatag attagctaat gagtgtgctc    1980
aagtattgag tgaaatggtc atgtgtggcg gttcactata tgttaaacca ggtggaacct    2040
catcaggaga tgccacaact gcttatgcta atagtgtttt taacatttgt caagctgtca    2100
cggccaatgt taatgcactt ttatctactg atggtaacaa aattgccgat aagtatgtcc    2160
gcaatttaca acacagactt tatgagtgtc tctatagaaa tagagatgtt gacacagact    2220
ttgtgaatga gttttacgca tatttgcgta aacatttctc aatgatgata ctctctgacg    2280
atgctgttgt gtgtttcaat agcacttatg catctcaagg tctagtggct agcataaaga    2340
actttaagtc agttctttat tatcaaaaca atgtttttat gtctgaagca aaatgttgga    2400
ctgagactga ccttactaaa ggacctcatg aatttttgctc tcaacataca atgctagtta    2460
aacagggtga tgattatgtg taccttcctt acccagatcc atcaagaatc ctaggggccg    2520
gctgttttgt agatgatatc gtaaaaacag atggtacact tatgattgaa cggttcgtgt    2580
ctttagctat agatgcttac ccacttacta aacatcctaa tcaggagtat gctgatgtct    2640
ttcatttgta cttacaatac ataagaaagc tacatgatga gttaacagga cacatgttag    2700
acatgtattc tgttatgctt actaatgata acacttcaag gtattgggaa cctgagtttt    2760
atgaggctat gtacacaccg catacagtct tacagg                             2796
```

```
<210> SEQ ID NO 3
<211> LENGTH: 249
<212> TYPE: DNA
<213> ORGANISM: Artificial Sequence
<220> FEATURE:
<223> OTHER INFORMATION: Synthetic Construct

<400> SEQUENCE: 3
tctaaactta cagatcttaa atgcacatct gtggttctcc tctctgtgct ccaacagtta     60
cacttagagg ctaatagtag ggcctgggct ttctgtgtta aatgccataa tgacatattg    120
gcagcaacag accccagtga ggctttcgag aaattcgtaa gtctctttgc cactttaatg    180 acttttctg gtaatgtaga tcttgatgcg ttagctagtg atattttttga cactcctagc    240 gtacttcaa                                                            249
```

```
<210> SEQ ID NO 4
<211> LENGTH: 249
<212> TYPE: DNA
<213> ORGANISM: Artificial Sequence
<220> FEATURE:
<223> OTHER INFORMATION: Synthetic Construct

<400> SEQUENCE: 4
tctaaaatgt cagatgtaaa gtgcacatca gtagtcttac tctcagtttt gcaacaactc     60
agagtagaat catcatctaa attgtgggct caatgtgtcc agttacacaa tgacattctc    120
ttagctaaag atactactga agcctttgaa aaaatggttt cactactttc tgttttgctt    180
tccatgcagg gtgctgtaga cataaacaag ctttgtgaag aaatgctgga caacagggca    240
```

```
accttacaa                                                            249

<210> SEQ ID NO 5
<211> LENGTH: 597
<212> TYPE: DNA
<213> ORGANISM: Artificial Sequence
<220> FEATURE:
<223> OTHER INFORMATION: Synthetic Construct

<400> SEQUENCE: 5
gctactcttt ctgagttttc acacttagct acctttgctg agttggaagc tgcgcagaaa      60
gcctatcagg aagctatgga ctctggtgac acctcaccac aagttcttaa ggctttgcag     120
aaggctgtta atatagctaa aaacgcctat gagaaggata aggcagtggc ccgtaagtta     180
gaacgtatgg ctgatcaggc tatgacttct atgtataagc aagcacgtgc tgaagacaag     240
aaagcaaaaa ttgtcagtgc tatgcaaact atgttgtttg gtatgattaa gaagctcgac     300
aacgatgttc ttaatggtat catttctaac gctaggaatg gttgtatacc tcttagtgtc     360
attccactgt gtgcttcaaa taaacttcgc gttgtaattc ctgacttcac cgtctggaat     420
caggtagtca catatccctc gcttaactac gctggggctt tgtgggacat tacagttata     480
aacaatgtgg acaatgaaat tgttaagtct tcagatgttg tagacagcaa tgaaaattta     540
acatggccac ttgttttaga atgcactagg gcatccactt ctgccgttaa gttgcaa       597

<210> SEQ ID NO 6
<211> LENGTH: 594
<212> TYPE: DNA
<213> ORGANISM: Artificial Sequence
<220> FEATURE:
<223> OTHER INFORMATION: Synthetic Construct

<400> SEQUENCE: 6
gctatagcct cagagtttag ttcccttcca tcatatgcag cttttgctac tgctcaagaa      60
gcttatgagc aggctgttgc taatggtgat tctgaagttg ttcttaaaaa gttgaagaag     120
tctttgaatg tggctaaatc tgaatttgac cgtgatgcag ccatgcaacg taagttggaa     180
aagatggctg atcaagctat gacccaaatg tataaacagg ctagatctga ggacaagagg     240
gcaaaagtta ctagtgctat gcagacaatg cttttcacta tgcttagaaa gttggataat     300
gatgcactca caacattat caacaatgca agagatggtt gtgttccctt gaacataata     360
cctcttacaa cagcagccaa actaatggtt gtcataccag actataacac atataaaaat     420
acgtgtgatg gtacaacatt tacttatgca tcagcattgt gggaaatcca acaggttgta     480
gatgcagata gtaaaattgt tcaacttagt gaaattagta tggacaattc acctaattta     540
gcatggcctc ttattgtaac agctttaagg gccaattctg ctgtcaaatt acag          594

<210> SEQ ID NO 7
<211> LENGTH: 1653
<212> TYPE: DNA
<213> ORGANISM: Artificial Sequence
<220> FEATURE:
<223> OTHER INFORMATION: Synthetic Construct

<400> SEQUENCE: 7
atggaagacg ccaaaaacat aaagaaaggc ccggcgccat tctatccgct ggaagatgga      60
accgctggag agcaactgca taaggctatg aagagatacg ccctggttcc tggaacaatt     120
gcttttacag atgcacatat cgaggtggac atcacttacg ctgagtactt cgaaatgtcc     180
gttcggttgg cagaagctat gaaacgatat gggctgaata caaatcacag aatcgtcgta     240
```

-continued

```
tgcagtgaaa actctcttca attctttatg ccggtgttgg gcgcgttatt tatcggagtt       300
gcagttgcgc ccgcgaacga catttataat gaacgtgaat tgctcaacag tatgggcatt       360
tcgcagccta ccgtggtgtt cgtttccaaa aaggggttgc aaaaaatttt gaacgtgcaa       420
aaaaagctcc caatcatcca aaaaattatt atcatggatt ctaaaacgga ttaccaggga       480
tttcagtcga tgtacacgtt cgtcacatct catctacctc ccggttttaa tgaatacgat       540
tttgtgccag agtccttcga tagggacaag acaattgcac tgatcatgaa ctcctctgga       600
tctactggtc tgcctaaagg tgtcgctctg cctcatagaa ctgcctgcgt gagattctcg       660
catgccagag atcctatttt tggcaatcaa atcattccgg atactgcgat tttaagtgtt       720
gttccattcc atcacggttt tggaatgttt actacactcg atatttgat atgtggattt        780 cgagtcgtct taatgtatag atttgaagaa gagctgtttc tgaggagcct tcaggattac       840
aagattcaaa gtgcgctgct ggtgccaacc ctattctcct tcttcgccaa aagcactctg       900
attgacaaat acgatttatc taatttacac gaaattgctt ctggtggcgc tcccctctct       960
aaggaagtcg gggaagcggt tgccaagagg ttccatctgc caggtatcag gcaaggatat      1020
gggctcactg agactacatc agctattctg attacacccg aggggggatga taaaccgggc     1080 gcggtcggta aagttgttcc attttttgaa gcgaaggttg tggatctgga taccgggaaa      1140
acgctgggcg ttaatcaaag aggcgaactg tgtgtgagag gtcctatgat tatgtccggt      1200
tatgtaaaca atccggaagc gaccaacgcc ttgattgaca aggatggatg gctacattct      1260
ggagacatag cttactggga cgaagacgaa cacttcttca tcgttgaccg cctgaagtct      1320
ctgattaagt acaaaggcta tcaggtggct cccgctgaat tggaatccat cttgctccaa      1380 cacccccaaca tcttcgacgc aggtgtcgca ggtcttcccg acgatgacgc cggtgaactt     1440
cccgccgccg ttgttgtttt ggagcacgga aagacgatga cggaaaaaga gatcgtggat      1500
tacgtcgcca gtcaagtaac aaccgcgaaa aagttgcgcg gaggagttgt gtttgtggac      1560
gaagtaccga aaggtcttac cggaaaactc gacgcaagaa aaatcagaga gatcctcata     1620
aaggccaaga agggcggaaa gatcgccgtg taa                                   1653
```

```
<210> SEQ ID NO 8
<211> LENGTH: 516
<212> TYPE: DNA
<213> ORGANISM: Artificial Sequence
<220> FEATURE:
<223> OTHER INFORMATION: Synthetic Construct

<400> SEQUENCE: 8
atggtcttca cactcgaaga tttcgttggg gactggcgac agacagccgg ctacaacctg        60
gaccaagtcc ttgaacaggg aggtgtgtcc agtttgtttc agaatctcgg ggtgtccgta       120
actccgatcc aaaggattgt cctgagcggt gaaaatgggc tgaagatcga catccatgtc       180
atcatcccgt atgaaggtct gagcggcgac caaatgggcc agatcgaaaa aattttttaag      240 gtggtgtacc ctgtggatga tcatcacttt aaggtgatcc tgcactatgg cacactggta       300
atcgacgggg ttacgccgaa catgatcgac tatttcggac ggccgtatga aggcatcgcc       360
gtgttcgacg gcaaaaagat cactgtaaca gggaccctgt ggaacggcaa caaaattatc       420
gacgagcgcc tgatcaaccc cgacggctcc ctgctgttcc gagtaaccat caacggagtg       480
accggctggc ggctgtgcga acgcattctg gcgtaa                                 516
```

CELL-BASED REPORTER ASSAY FOR SCREENING INHIBITORS OF CORONAVIRUS RNA-DEPENDENT RNA POLYMERASE ACTIVITY

CROSS REFERENCE TO RELATED APPLICATIONS

This application is a United States National Phase Patent Application of International Patent Application Number PCT/KR2020/013330, filed on Sep. 29, 2020, which claims the benefit of priority to KR Application No. 10-2020-0008687, filed Jan. 22, 2020, which are incorporated by reference herein in their entirety.

REFERENCE TO AN ELECTRONIC SEQUENCE LISTING

The content of the electronic sequence listing submitted on Apr. 19, 2023 as a text file named "11254-005US1 2023_04_19 Sequence Listing.txt" created on Apr. 19, 2023 and having a size of 13.4 KB is hereby incorporated by reference in its entirety pursuant to 37 CFR 1.52(e)(5).

TECHNICAL FIELD

The present invention relates to a screening system for a therapeutic agent for coronavirus infection. More particularly, the present invention relates to a screening composition for a therapeutic agent for coronavirus infection including a CoV RdRp expression vector and a bicistronic reporter vector, and a screening kit for a therapeutic agent for coronavirus infection including the composition, and a method for screening a therapeutic agent for coronavirus infection using the composition or kit.

BACKGROUND ART

Coronavirus disease 2019 (COVID-19) is a virus first discovered in Wuhan City, Hubei Province, China in 2019 and belongs to the family of Coronaviridae. It is known as a virus similar to SARS-CoV (severe acute respiratory syndrome coronavirus) and Middle East respiratory syndrome coronavirus (MERS-CoV). Although no clear source of infection and path of infection have been identified, it has been reported that the possibility of infection through contact with bats in the Wuhan area is high and transmission through close contact between humans is possible. Although the source of infection and the route of infection have not yet been confirmed, it has been reported that infection is highly likely through contact with bats in the Wuhan area, and transmission is possible through close person-to-person contact. In addition, COVID-19 has an incubation period of about 2 weeks and mainly shows respiratory symptoms such as cough accompanied by fever, difficulty breathing, shortness of breath, and sputum. In addition to headache, chills, runny nose, and muscle pain, loss of appetite, nausea, and vomiting, digestive symptoms such as abdominal pain and diarrhea may appear.

Middle East respiratory syndrome (MERS) is a respiratory disease caused by MERS coronavirus (MERS-CoV) infection. It is transmitted from animals such as dromedaries and bats to humans and exhibits a mortality rate of up to 38%.

The coronavirus (CoV), which causes the infection, is a virus belonging to the genus *Betacoronavirus*, and contains a 30.1 kb large-sense single-stranded RNA genome expressing both structural and non-structural proteins. The CoV RNA is introduced into the host cell to deliver two polyproteinaceous genes (pp1a and pp1ab) that can be transcribed into 16 non-structural proteins (NSPs) required for viral replication and transcription. CoV polyproteins are self-cleaved with papain-like proteases (PLpro) and 3C-like proteases (3CLpro), followed by expression of the replication enzymes RNA-dependent RNA polymerase (RdRp), helicase, and exonuclease.

Among the above enzymes, RNA-dependent RNA polymerase (RdRp) is a 106.9 kDa protein encoded by the nsp12gene expressed early in the infection process and is known to have a very important role in viral replication, attracting attention as a major target for antiviral therapy. For example, a helicase inhibitor developed to treat infection of acute respiratory syndrome coronavirus (SARS-CoV) is known to inhibit the replication of SARS-CoV by inhibiting the function of RdRp.

Meanwhile, nucleoside analogues target proteins for viral replication, particularly viral DNA or RNA polymerase, and are known to be effective in treating many viral infections.

For example, hepatitis C virus (HCV) RdRp inhibitors show high success rates in clinical treatment, Ribavirin triphosphate is known to inhibit HCV RdRp, and Sofosbuvir is known as a nucleotide analogue that is introduced into HCV RNA by NS5B polymerase.

Recently, various studies are being conducted to treat COVID-19, which has become a global problem. For example, Remdesivir, approved as a treatment for COVID-19, is known as a broad-spectrum coronavirus RdRp inhibitor. As such, even though the coronavirus RdRp is also a major target of a candidate drug for treating coronavirus infection, there is no precedent for developing a cell-based reporter system capable of efficient screening of a candidate drug targeting the coronavirus RdRp (Reference: Korea Patent Publication No. 2002-0010241; Korean Patent Publication No. 2016-0138943; U.S. Patent Publication No. 2019-0030187).

DISCLOSURE

Technical Problem

The present inventors have made intensive research efforts to develop a method for more effectively discovering candidate drugs that can prevent or treat MERS-CoV infection. As a result, when a bicistronic reporter vector for measuring RdRp activity containing two types of luciferase genes (FLuc, RLuc) is used, it was confirmed that candidate drugs that can affect RdRp activity can be more effectively discovered, thereby completing the present invention.

Technical Solution

The main object of the present invention is to provide a screening composition for a therapeutic agent for coronavirus infection, comprising a CoV RdRp expression vector and a bicistronic reporter vector.

Another object of the present invention is to provide a screening kit for a therapeutic agent for coronavirus infection comprising the composition.

Still another object of the present invention is to provide a method for screening a therapeutic agent for coronavirus infection using the composition or kit.

Yet another object of the present invention is to provide the use of the composition for screening of a therapeutic agent for coronavirus infection.

Advantageous Effects

When the screening composition for a therapeutic agent for coronavirus infection, provided by the present invention, is used, candidate materials that can have direct influences on the activity of CoV RdRp can be screened more quickly and easily, and thus, the composition can be widely used in the development of therapeutic agents for coronavirus infection.

BRIEF DESCRIPTION OF DRAWINGS

FIG. 1 is a schematic diagram showing the structure of a reporter vector used in a cell-based CoV RdRp activity reporter assay.

FIG. 2a is a diagram of Western blot analysis showing the result of analyzing the level of the N-terminal or C-terminal FLAG MERS-CoV RdRp expressed in HEK293T cells into which recombinant vector pN-termFlag-nsp12(MERS-CoV) or pC-termFlag-nsp12(MERS-CoV) was introduced.

FIG. 2b is a graph showing the result of comparing the NLuc activity measured in the N-terminal or C-terminal FLAG MERS-CoV RdRp expressed in HEK293T cells into which recombinant vector pN-termFlag-nsp12(MERS-CoV) or pC-termFlag-nsp12(MERS-CoV) was introduced.

FIG. 2c a graph showing the results of comparing the FLuc activity, NLuc activity, and NLuc/FLuc ratio derived from the N-terminal FLAG MERS-CoV RdRp expressed in HEK293T cells into which (+)FLuc-(−)UTR-NLuc and pN-termFlag-nsp12(MERS-CoV) with or without anti-sense HCV IRES were introduced.

FIG. 2d is a diagram of Western blot analysis showing the results of analyzing the levels of N-terminal FLAG-labeled MERS-CoV RdRp, C-terminal FLAG-labeled MERS-CoV NSP7 and C-terminal FLAG-labeled MERS-CoV NSP8 expressed in HEK293T cells into which recombinant vectors pN-termFlag-nsp12(MERS-CoV), pC-termFlag-nsp7 (MERS-CoV) and pC-termFlag-nsp8(MERS-CoV) containing MERS-CoV-derived genes were introduced.

FIG. 2e is a graph showing the result of confirming the effect of MERS-CoV NSP7/MERS-CoV NSP8 or C-terminal FLAG-labeled MERS-CoV NSP7/MERS-CoV NSP8 on the activity of N-terminal FLAG-labeled MERS-CoV RdRp.

FIG. 3a is a diagram of Western blot analysis showing the result of analyzing the expression levels of SARS-CoV-2 NSP7, SARS-CoV-2 NSP8, N-terminal FLAG-labeled SARS-CoV-2 RdRp or C-terminal FLAG-labeled SARS-CoV-2 RdRp expressed in HEK293T cells into which recombinant vectors p-nsp7(SARS-CoV-2), p-nsp8(SARS-CoV-2), pN-termFlag-nsp12(SARS-CoV-2) or pC-term Flag-nsp12(SARS-CoV-2) was introduced.

FIG. 3b is a graph showing the result of comparing the NLuc activity derived from the N-terminal or C-terminal FLAG SARS-CoV-2 RdRp protein expressed in HEK293T cells into which recombinant vector pN-termFlag-nsp12 (SARS-CoV-2) or pC-termFlag-nsp12 (SARS-CoV-2) was introduced.

FIG. 3c is a graph showing the results of confirming whether SARS-CoV-2 NSP7 or SARS-CoV-2 NSP8 affects the activity of N-terminal FLAG-labeled SARS-CoV-2 RdRp.

FIG. 3d is a graph showing the result of comparing the NLuc/FLuc ratio derived from the N-terminal FLAG-labeled SARS-CoV-2 RdRp expressed in each HEK293T cell into which p(+)FLuc-(−)UTR-NLuc and pN-termFlag-nsp12(SARS-CoV-2) containing polyA of (−)3'-UTR (w/A33) or not containing polyA (w/o A33) were introduced and various levels of SARS-CoV-2 RdRp were introduced.

FIG. 4a is a graph showing the evaluation results using various concentrations of ribavirin in the cell-based MERS-CoV RdRp activity reporter assay system.

FIG. 4b is a graph showing the evaluation results using various concentrations of sofosbuvir in the cell-based MERS-CoV RdRp activity reporter assay system.

FIG. 4c is a graph showing the evaluation results using various concentrations of favipiravir in the cell-based MERS-CoV RdRp activity reporter assay system.

FIG. 4d is a graph showing the evaluation results using various concentrations of lamivudine in the cell-based MERS-CoV RdRp activity reporter assay system.

FIG. 4e is a graph showing the evaluation results using various concentrations of zidovudine in the cell-based MERS-CoV RdRp activity reporter assay system.

FIG. 4f is a graph showing the evaluation results using various concentrations of valacyclovir in the cell-based MERS-CoV RdRp activity reporter assay system.

FIG. 4g is a graph showing the evaluation results using various concentrations of vidarabine in the cell-based MERS-CoV RdRp activity reporter assay system.

FIG. 5a is a schematic diagram showing the chemical structure of dasabuvir.

FIG. 5b is a graph showing the results of comparing the cell viability of HEK293T cells treated with various concentrations of dasabuvir.

FIG. 5c is a graph showing the evaluation results using various concentrations of dasabuvir in the cell-based MERS-CoV RdRp activity reporter assay system.

FIG. 5d is a graph showing the results of performing non-linear regression analysis on the results of dasabuvir used in the cell-based MERS-CoV RdRp activity reporter assay system.

FIG. 6a is a schematic diagram showing the chemical structure of remdesivir.

FIG. 6b is a graph showing the results of comparing the cell viability of HEK293T cells treated with various concentrations of remdesivir.

FIG. 6c is a graph showing the evaluation results using various concentrations of remdesivir in a cell-based MERS-CoV RdRp activity reporter assay system.

FIG. 6d is a graph showing the results of performing non-linear regression analysis on the results of remdesivir used in the cell-based MERS-CoV RdRp activity reporter assay system.

FIG. 7a is a graph showing the evaluation results using various concentrations of remdesivir in the cell-based SARS-CoV-2 RdRp activity reporter assay system.

FIG. 7b is a graph showing the results of performing non-linear regression analysis on the results of remdesivir used in the cell-based SARS-CoV-2 RdRp activity reporter assay system.

FIG. 8 is a graph showing the analysis results using the Z-factor and Z'-factor values of the screening composition for a therapeutic agent for Middle East respiratory syndrome provided by the present invention.

DETAILED DESCRIPTION OF PREFERRED EMBODIMENTS

One embodiment of the present invention for achieving the above objects provides a screening composition for a therapeutic agent for coronavirus infection, including:

(a) a CoV RdRp expression vector including a FLAG-labeled CoV (coronavirus) nsp12 gene at the N-terminus or C-terminus; and (b) a bicistronic reporter vector including: a firefly luciferase gene in the sense direction ((+)FLuc) and a NanoLuc luciferase gene in the antisense direction ((−)NLuc); wherein the (−)NLuc forms domains (3'-UTR, NLuc and 5'-UTR) interposed between 3'-UTR and 5'-UTR in the antisense direction derived from CoV; wherein the 3'-UTR, NLuc, and 5'-UTR domains in the antisense direction are in the form in which a ribozyme self-cleavage sequence derived from hepatitis delta virus (HDV) is bound to each of the 5'- and 3'-ends thereof; and a firefly luciferase gene in the sense direction independently of the domain in the antisense direction.

The present inventors applied a known cell-based HCV RdRp activity assay system to develop a screening composition for a therapeutic agent for coronavirus infection including a CoV RdRp expression vector and a reporter vector, and the known cell-based HCV RdRp activity assay system and the screening composition for a therapeutic agent for coronavirus infection show three major differences: one is that the composition is used in a method for screening a therapeutic agent for treating coronavirus infection, such as MERS-CoV or SARS-CoV-2, another is that the N-terminal or C-terminal of the CoV nsp12 gene included in the CoV RdRp expression vector is FLAG-labeled, and still another is that it does not include an internal ribosome entry site (IRES) at the end of the 5'-UTR. When the N-terminal or C-terminal FLAG-labeled MERS-CoV nsp12 gene or a 5'-UTR that does not include the IRES is used, there is an advantage in that the activity of the NLuc included in the reporter vector is increased.

In addition, the CoV RdRp expression vector may further include a CoV nsp7 gene or a CoV nsp8 gene as well as a CoV nsp12gene, and the NLuc activity included in the reporter vector may be increased by the added genes.

As used herein, the term "CoV nsp12 gene" refers to a gene encoding RNA-dependent RNA polymerase (RdRp), a replication enzyme of coronavirus.

In the present invention, as the CoV nsp12 gene, a MERS-CoV nsp12 gene or a SARS-CoV-2 nsp12 gene may be used. The specific nucleotide sequences of these CoV nsp12 genes or the amino acid sequence information of the proteins are reported in a database such as NCBI. For example, it is reported as GenBank Accession Nos. KT029139 13410-16207 nt (MERS-CoV) or MN908947.3 13442-16237 nt (SARS-CoV-2).

In the present invention, the nucleotide sequence of SEQ ID NO: 1 was used as the nsp12 gene derived from MERS-CoV, and the nucleotide sequence of SEQ ID NO: 2 was used as the nsp12 gene derived from SARS-CoV-2.

The CoV RdRp expression vector provided in the present invention includes N-terminal or C-terminal FLAG-labeled CoV nsp12genes (MERS-CoV nsp12 gene or SARS-CoV-2 nsp12 gene) at the N-terminus or C-terminus, but it may include the N-terminal FLAG-labeled CoV nsp12 gene because the effect is relatively superior when the N-terminal FLAG-labeled CoV nsp12 gene is included rather than the C-terminal FLAG-labeled CoV nsp12 gene.

In addition, the CoV RdRp expression vector provided in the present invention may further include a CoV nsp7 gene, a CoV nsp8 gene, etc. alone or in combination in addition to the CoV nsp12 gene.

As used herein, the term "CoV nsp7gene" refers to a gene encoding the NSP7 protein of coronavirus.

In the present invention, as the CoV nsp7 gene, a MERS-CoV nsp7 gene or a SARS-CoV-2 nsp7 gene may be used. The specific nucleotide sequences of these CoV nsp7 genes or the amino acid sequence information of the proteins are reported in a database such as NCBI. For example, it is reported as GenBank Accession Nos. KT029139 11814-12062 nt (MERS-CoV) or MN908947.3 11843-12091 nt (SARS-CoV-2).

In the present invention, the nucleotide sequence of SEQ ID NO: 3 was used as the nsp7 gene derived from MERS-CoV, and the nucleotide sequence of SEQ ID NO: 4 was used as the nsp7 gene derived from SARS-CoV-2.

As used herein, the term "CoV nsp8 gene" refers to a gene encoding the NSP8 protein of coronavirus.

In the present invention, as the CoV nsp8 gene, a MERS-CoV nsp8 gene or a SARS-CoV-2 nsp8 gene may be used. The specific nucleotide sequences of these CoV nsp8 genes or the amino acid sequence information of the proteins are reported in a database such as NCBI. For example, it is reported as GenBank Accession Nos. KT029139 12063-12659 nt (MERS-CoV) or MN908947.3 12092-12685 nt (SARS-CoV-2).

In the present invention, the nucleotide sequence of SEQ ID NO: 5 was used as the nsp8 gene derived from MERS-CoV, and the nucleotide sequence of SEQ ID NO: 6 was used as the nsp8 gene derived from SARS-CoV-2.

The CoV nsp7 gene and CoV nsp8 gene may be used in a form introduced into the CoV RdRp expression vector together with the CoV nsp12 gene, or in a form introduced with the CoV RdRp expression vector containing the CoV nsp12 gene as it is included in a separate expression vector.

As used herein, the term "firefly luciferase gene (FLuc)" refers to a gene encoding luciferase, which is a major enzyme that exhibits luminescence in fireflies.

The specific nucleotide sequence of the FLuc or amino acid sequence information of the protein is reported in a database such as NCBI. For example, it is reported as GenBank Accession Nos. U47295.2 88-1740 nt, etc.

In the present invention, the nucleotide sequence of SEQ ID NO: 7 was used as the FLuc gene.

As used herein, the term "NanoLuc luciferase gene (NLuc)" refers to a gene encoding an artificially synthesized luciferase variant.

The specific nucleotide sequence of the NLuc or the amino acid sequence information of the protein is reported in a database such as the NCBI. For example, it is reported as GenBank Accession No. KM359770.1 577-1092 nt, etc.

In the present invention, the nucleotide sequence of SEQ ID NO: 8 was used as the NLuc gene.

The reporter vector provided in the present invention includes a FLuc gene in the sense direction and an NLuc gene in the antisense direction in order to prevent expression of both luciferases by one promoter.

First, when a CoV RdRp expression vector and a reporter vector are introduced together into a host cell, the entire sequence of the CoV RdRp expression vector and the reporter vector is transcribed by the DNA-dependent RNA polymerase Pol II of the host cell to form each transcriptome. The transcriptome of the CoV RdRp expression vector is translated to biosynthesize CoV RdRp, whereas the transcriptome of the reporter vector is physically separated from the FLuc gene and the NLuc gene by the ribozyme self-cleavage sequence contained therein. The FLuc gene is expressed at a transcribed level and can be used as an internal control, whereas the NLuc gene is replicated by the previously expressed CoV RdRp, and the level of fluorescence is proportional to the level of replication. At this time, when the host cell is treated with a candidate material that inhibits the activity of CoV RdRp, the activity of CoV RdRp is reduced thereby, and the reduced activity of CoV RdRp is the cause of reducing the color development level of the luminescent protein expressed from NLuc. Therefore, it can be confirmed whether the treated candidate material can inhibit the activity of CoV RdRp by the color development level of the luminescent protein expressed from NLuc.

In the present invention, the screening composition for a therapeutic agent for coronavirus infection may each independently include a CoV RdRp expression vector and a reporter vector, or may include a transfectant into which the CoV RdRp expression vector and the reporter vector are introduced.

That is, when the composition each independently includes the CoV RdRp expression vector and the reporter vector, it can be confirmed whether the candidate material can inhibit the activity of CoV RdRp by introducing the two vectors into the desired host cell and treating with the candidate material expected to inhibit the activity of CoV RdRp. When using the composition in such form, it is possible to more easily screen candidate materials capable of inhibiting the activity of CoV RdRp expressed in animal cells.

In addition, in the case of the transfectant introduced with the two vectors, it can be confirmed whether the candidate material can inhibit the activity of CoV RdRp by culturing the transfectant and measuring the fluorescence level expressed therefrom, and treating the transfectant with a candidate material expected to inhibit the activity of CoV RdRp, followed by measuring the change in the fluorescence level. When using the composition in such form, a large number of candidate materials can be screened more rapidly.

According to one embodiment of the present invention, it was confirmed whether various nucleoside derivatives (ribavirin, sofosbuvir, favipiravir, lamivudine, zidovudine, vidarabine, valacyclovir, dasabuvir, remdesivir, etc.) can inhibit the activity of MERS-CoV RdRp by using the screening composition for a therapeutic agent for coronavirus infection. As a result, it was confirmed that ribavirin, sofosbuvir, favipiravir, lamivudine, zidovudine, vidarabine, and valacyclovir had no significant effect on the activity of MERS-CoV RdRp (FIGS. 4a to 4g), dasabuvir reduced the activity of MERS-CoV RdRp by about 50% (FIGS. 5c and 5d), and remdesivir was able to inhibit MERS-CoV RdRp activity in a concentration-dependent manner (FIGS. 6c and 6d), and it was also confirmed that SARS-CoV-2 RdRp activity was also inhibited in a concentration-dependent manner (FIGS. 7a and 7b).

Another embodiment of the present invention provides a screening kit for a therapeutic agent for coronavirus infection, including the screening composition for a therapeutic agent for coronavirus infection above.

The above-described screening composition for a therapeutic agent for coronavirus infection and each component included therein are the same as described above.

The screening kit for a therapeutic agent for coronavirus infection provided by the present invention may further include additional components that can be used to utilize the composition more effectively as well as the screening composition for a therapeutic agent for coronavirus infection.

The additional components may include a host cell, a medium for culturing the host cell, the host cell culture vessel, a buffer for introducing each vector included in the screening composition into the host cell, an optical measuring device for measuring the fluorescence level of luciferase expressed using the composition, software for analyzing the measured fluorescence level, a hardware system equipped with the software, etc.

Still another embodiment of the present invention provides a method for screening a therapeutic agent for coronavirus infection using the composition or kit.

More specifically, the method for screening a therapeutic agent for coronavirus infection provided by the present invention may include the steps of:

(a) preparing a transfectant into which a CoV RdRp expression vector and a reporter vector included in the screening composition for a therapeutic agent for coronavirus infection above are introduced together;

(b) treating the prepared transfectant with a candidate material expected to inhibit the activity of coronavirus-derived RNA-dependent RNA polymerase (CoV RdRp); and (c) measuring the fluorescence level derived from Nano-Luc luciferase after treating the candidate material.

In step (a), when the screening composition for a therapeutic agent for coronavirus infection independently includes a CoV RdRp expression vector and a reporter vector, each vector should be introduced into a host cell to prepare a transfectant, and when the composition is in a form including the transfectant introduced with the CoV RdRp expression vector and the reporter vector, the transfectant included in the composition can be used as it is.

In addition, as described above, the CoV RdRp expression vector may be in the form of a MERS-CoV RdRp expression vector containing a MERS-CoV nsp12 gene or a SARS-CoV-2 RdRp expression vector containing a SARS-CoV-2 nsp12 gene, or may further include the nsp7 gene (MERS-CoV nsp7 gene or SARS-CoV-2 nsp7 gene) or nsp8 gene (MERS-CoV nsp8 gene or SARS-CoV-2 nsp8 gene) alone or in combination, in addition to the nsp12 gene.

In step (b), a step of pre-measuring the fluorescence level derived from NanoLuc luciferase, which is stably maintained in a state in which the candidate material is not treated by culturing the transfectant before treatment with the candidate material, may be additionally included. Further, it may further include a step of pre-measuring the fluorescence level derived from firefly luciferase as an internal control.

In step (c), when the fluorescence level derived from NanoLuc luciferase is reduced after treating the candidate material, it can be expected that the treated candidate material can inhibit the activity of CoV RdRp (MERS-CoV RdRp or SARS-CoV-2 RdRp), and such candidate material can be used in the development of therapeutic agents for coronavirus infection.

However, in step (c), it is necessary to confirm whether the fluorescence level derived from the firefly luciferase, which is an internal control, is changed. If the fluorescence level derived from the firefly luciferase is rapidly changed after treating the candidate material, it is necessary to confirm whether the effect of the candidate substance is caused by the cytotoxicity exhibited by the candidate material.

Yet another embodiment of the present invention provides the use of the composition for screening therapeutic agents for coronavirus infection.

MODE FOR CARRYING OUT THE INVENTION

The present invention will be described in detail by way of Examples. However, these Examples are given for illustrative purposes only, and are not intended to limit the scope of the invention thereto.

Example 1

Development of Cell-Based CoV RdRp Activity Reporter Assay System

To develop a cell-based CoV RdRp activity reporter assay by modifying the known cell-based HCV RdRp activity assay, a reporter vector and an RdRp expression vector targeting MERS-CoV or SARS-CoV-2, a type of CoV, were developed, respectively, and their efficacy was evaluated.

Example 1-1

Construction of Reporter Vector

By modifying the known bicistronic HCV RdRp reporter vector, a reporter vector was constructed.

FLuc (firefly luciferase gene, GenBank Accession No. U47295, SEQ ID NO: 7) in the sense direction from pGL3-basic was amplified by way of PCR and introduced into pcDNA3.1(+) vector to prepare a recombinant vector.

Through GENEWIZ, HDV ribozyme sequence, antisense 3'-UTR (untranslated region) of CoV, antisense Nano-glo® luciferase gene (NLuc) (Promega Corporation, GenBank Accession No. KM359770, SEQ ID NO: 8), antisense 5'-UTR (with/without HCV IRES sequence) of CoV and HDV ribozyme sequence were sequentially synthesized and introduced downstream of the (+)FLuc gene of the recombinant vector to prepare a recombinant vector, i.e., p(+)FLuc-(−)UTR-NLuc reporter vector (with or without the antisense HCV IRES sequence between (−)5'-UTR and (−)NLuc sequence) was constructed (FIG. 1).

FIG. 1 is a schematic diagram showing the structure of a reporter vector used in the cell-based CoV RdRp activity reporter assay.

As shown in FIG. 1, the bicistronic reporter vector p(+)FLuc-(−)UTR-NLuc used in the cell-based CoV RdRp activity reporter assay includes the firefly luciferase gene in the sense direction ((+)FLuc), Nano-glo® luciferase gene in the antisense direction ((−)NLuc) located between antisense 3'- and 5'-UTR of CoV, and a ribozyme self-cleavage sequence of hepatitis delta virus (HDV).

The entire sequence of the bicistronic (+)FLuc-(−)UTR-NLuc RNA is transcribed by the DNA-dependent RNA polymerase Pol II of the host cell, and the transcript produced through the transcription is cleaved by HDV ribozyme self-cleavage sequence, and NLuc located between the antisense 3'- and 5'-UTR RNA shows activity as +sense RNA synthesized by CoV RdRp is translated into NLuc, so the expression level of NLuc is proportional to the activity level of CoV RdRp.

Meanwhile, the expression level of FLuc is used as an internal control of transcription/translation to minimize variation between samples.

Example 1-2

Construction of MERS-CoV RdRp Expression Vector and Efficacy Evaluation

An RdRp expression vector targeting MERS-CoV, a type of CoV, was developed, and the efficacy of the RdRp expression vector was evaluated in transfectant s expressed together with the previously prepared reporter vector.

Example 1-2-1

Construction of MERS-CoV RdRp Expression Vector

First, in order to express MERS-CoV RdRp, a type of CoV RdRp, in human cell lines, the present inventors constructed a human codon-optimized FLAG-labeled MERS-CoV nsp12 vector.

Since the N-terminus of the poliovirus RdRp is important for protein folding and localization of the active site, it is known that the heterologous sequence of the N-terminus affects polymerase activity.

Roughly, FLAG-labeled MERS-CoV nsp12 gene (Gen-Bank® Accession No. KT029139) at the N-terminus or C-terminus was synthesized in a human codon-optimized form and introduced into pcDNA3.1(+) vector to construct recombinant vector pN-termFlagnsp12 (MERS-CoV) or pC-termFlag-nsp12 (MERS-CoV), respectively.

It was confirmed whether the expression of MERS-CoV RdRp was possible using the above constructed recombinant vector.

First, HEK293T cells were inoculated in DMEM medium containing 10% FBS and 1% penicillin/streptomycin, and cultured at 37° C. and 5% $CO_2$ conditions.

Then, the HEK293T cells were inoculated into a 96-well plate, cultured overnight, and a mixture of TransIT®-LT1 transfection reagent (Mirus Bio LLC, Madison, WI, USA) and a recombinant vector was added thereto and cultured to obtain transformed cells.

The thus-obtained transformed cells were disrupted to obtain the cell lysates, respectively. Western blot analysis was performed using each of the cell lysates obtained above, an anti-FLAG antibody (Abcam plc, Cambridge, UK) and an HRP-conjugated secondary antibody (Abcam plc), and the result obtained therefrom was analyzed using an Enhanced Chemiluminescence Western Blotting Substrate (Thermo Fisher Scientific, Waltham, MA, USA) and Chemi-Doc™ Touch Imaging System (Bio-Rad Laboratories) (FIG. 2a).

FIG. 2a is a diagram of Western blot analysis showing the result of analyzing the level of the N-terminal or C-terminal FLAG MERS-CoV RdRp expressed in HEK293T cells into which recombinant vector pN-termFlag-nsp12(MERS-CoV) or pC-termFlag-nsp12(MERS-CoV) was introduced.

As shown in FIG. 2a, it was confirmed that the N-terminal or C-terminal FLAG MERS-CoV RdRp of approximately 110 kDa was expressed in HEK293T cells introduced with recombinant vector pN-termFlag-nsp12(MERS-CoV) or pC-termFlag-nsp12(MERS-CoV).

In addition, to compare the activity of N-terminal or C-terminal FLAG-labeled MERS-CoV RdRp, the luminescence level was measured in HEK293T cells transfected with p(+)FLuc-(−)UTR-NLuc (FIG. 2b).

FIG. 2b is a graph showing the result of comparing the NLuc activity measured in the N-terminal or C-terminal FLAG MERS-CoV RdRp expressed in HEK293T cells into which recombinant vector pN-termFlag-nsp12(MERS-CoV) or pC-termFlag-nsp12(MERS-CoV) was introduced.

As shown in FIG. 2b, the relative NLuc activity was increased by the expression of N-terminal or FLAG-labeled MERS-CoV RdRp in a dose-dependent manner, and the luciferase activity was similar.

Accordingly, the present inventors confirmed that the N-terminal FLAG label does not interfere with the activity of MERS-CoV RdRp.

Further, it was confirmed that the relative NLuc activity of the N-terminal FLAG-labeled MERS-CoV RdRp (5.91±0.14-fold with 80 ng of plasmid) showed a significantly higher level than the C-terminal FLAG-labeled MERS-CoV RdRp (3.9±0.26-fold with 80 ng of plasmid).

According to the above results, it can be seen that the pN-termFlag-nsp12 (MERS-CoV) plasmid is preferably used as the MERS-CoV RdRp expression vector used in the cell-based MERS-CoV RdRp activity reporter assay system.

Example 1-2-2

Optimization of Reporter Vector

The HCV 5'-UTR, which was used in the known cell-based HCV RdRp activity assay, contained an internal ribosome entry site (IRES), which is important for protein translation of the second cistronic luciferase after HCV NSSB polymerase replicated the positive-stranded luciferase RNA.

Since the present inventors used CoV 5'-UTR for the CoV RdRp reporter assay, they constructed p(+)FLuc-(–)UTR-NLuc with or without antisense HCV IRES between (–)5'-UTR and (–)NLuc sequences, and then the relative NLuc activity of MERS-CoV RdRp was compared (FIG. 2c).

FIG. 2c a graph showing the results of comparing the FLuc activity, NLuc activity, and NLuc/FLuc ratio derived from the N-terminal FLAG MERS-CoV RdRp expressed in HEK293T cells into which (+)FLuc-(–)UTR-NLuc with or without anti-sense HCV IRES and pN-termFlag-nsp12 (MERS-CoV) were introduced.

As shown in FIG. 2c, when p(+)FLuc-(–)UTR-NLuc with or without antisense HCV IRES and pN-termFlag-nsp12 (MERS-CoV) were introduced into HEK293T cells, the relative NLuc activity was reduced when p(+)FLuc-(–)UTR-NLuc and the HCV IRES plasmid were introduced together, compared to when p(+)FLuc-(–)UTR-NLuc without antisense HCV IRE was introduced.

Therefore, it could be seen that the MERS-CoV 5'-UTR does not require the HCV IRES sequence to translate the NLuc protein.

Example 1-2-3

Effect of nsp7 and nsp8 on MERS-CoV RdRp Activity

It was confirmed whether NSP7 and NSP8 derived from MERS-CoV could affect the MERS-CoV RdRp activity expressed from the pN-termFlag-nsp12 (MERS-CoV).

First, nsp7 gene, C-termFlag-nsp7 gene, nsp8 gene, and C-termFlag-nsp8 gene were obtained from the C-terminal FLAG-labeled or unlabeled MERS-CoV genomic gene (GenBank Accession No. KT029139), respectively, and each of the obtained genes was introduced into pcDNA3.1 (+) vector to construct recombinant vectors p-nsp7(MERS-CoV), pC-termFlag-nsp7(MERS-CoV), p-nsp8(MERS-CoV), and pC-termFlag-nsp8(MERS-CoV).

Using the method of Example 1-2, transfectant s containing pC-termFlag-nsp7 (MERS-CoV) and pC-termFlag-nsp8 (MERS-CoV) among each of the recombinant vectors and the previously constructed recombinant vector pN-term-Flag-nsp12(MERS-CoV) were obtained, and the expression level of the N-terminal FLAG-labeled MERS-CoV RdRp, C-terminal FLAG-labeled MERS-CoV NSP7, and C-terminal FLAG-labeled MERS-CoV NSP8 was confirmed therefrom by Western blot analysis (FIG. 2d).

FIG. 2d is a diagram of Western blot analysis showing the results of analyzing the levels of N-terminal FLAG-labeled MERS-CoV RdRp, C-terminal FLAG-labeled MERS-CoV NSP7, and C-terminal FLAG-labeled MERS-CoV NSP8 expressed in HEK293T cells into which recombinant vectors pN-termFlag-nsp12(MERS-CoV), pC-termFlag-nsp7 (MERS-CoV), and pC-termFlag-nsp8(MERS-CoV) containing MERS-CoV-derived genes were introduced.

As shown in FIG. 2d, the expression of N-terminal FLAG-labeled MERS-CoV RdRp and C-terminal FLAG-labeled MERS-CoV NSP8 was confirmed, but the expression of C-terminal FLAG-labeled MERS-CoV NSP7 was not confirmed.

Meanwhile, with respect to the activity of N-terminal FLAG-labeled MERS-CoV RdRp, it was confirmed whether C-terminal FLAG-labeled MERS-CoV NSP7 and C-terminal FLAG-labeled MERS-CoV NSP8 had an effect thereon.

Roughly, (a) transfectant s in which the p(+)FLuc-(–) UTR-NLuc reporter vector prepared in Example 1-1 and the recombinant vector pN-termFlag-nsp12(MERS-CoV) prepared above were introduced into HEK293T cells; (b) transfectant s in which p(+)FLuc-(–)UTR-NLuc reporter vector, pN-termFlag-nsp12(MERS-CoV), p-nsp7(MERS-CoV), and p-nsp8(MERS-CoV) were introduced into HEK293T cells; and (c) transfectant s in which p(+)FLuc-(–)UTR-NLuc reporter vector, pN-termFlag-nsp12(MERS-CoV), pC-termFlag-nsp7(MERS-CoV), and pC-termFlag-nsp8 (MERS-CoV) were introduced into the HEK293T cells were prepared, and the luminescence level was measured and compared from each transfectant (FIG. 2e). At this time, as a control, a transfectant in which the p(+)FLuc-(–)UTR-NLuc reporter vector was introduced into HEK293T cells was used.

FIG. 2e is a graph showing the result of confirming the effect of MERS-CoV NSP7/MERS-CoV NSP8 or C-terminal FLAG-labeled MERS-CoV NSP7/MERS-CoV NSP8 on the activity of N-terminal FLAG-labeled MERS-CoV RdRp.

As shown in FIG. 2e, it was confirmed that even when MERS-CoV NSP7/MERS-CoV NSP8 or C-terminal FLAG-labeled MERS-CoV NSP7/MERS-CoV NSP8 was expressed together, there was no change in the activity of N-terminal FLAG-labeled MERS-CoV RdRp.

Based on the results, it can be seen that p(+)FLuc-(–) UTR-NLuc without antisense HCV IRES and pN-termFlag-nsp12 are preferably used as the cell-based MERS-CoV RdRp activity reporter assay system.

Example 1-3

Construction of SARS-CoV-2 RdRp Expression Vector and Efficacy Evaluation

An RdRp expression vector targeting SARS-CoV-2, a type of CoV, was developed, and the efficacy of the RdRp expression vector was evaluated in the transfectant expressed together with the previously prepared reporter vectors.

Example 1-3-1

Construction of SARS-CoV-2 RdRp Expression Vector

First, from the genomic gene of SARS-CoV-2 (GenBank Accession No. MN908947.3) with or without FLAG-labeled C-terminus, the nsp7 gene, the nsp8 gene, and the N-terminus or C-terminus FLAG-labeled SARS-CoV-2 nsp12 gene were obtained, and each of the obtained genes was introduced into pcDNA3.1(+) vector to prepare each of the recombinant vectors p-nsp7(SARS-CoV-2), p-nsp8(SARS-CoV-2), pN-termFlag-nsp12(SARS-CoV-2), and pC-termFlag-nsp12(SARS-CoV-2).

Each of the recombinant vectors prepared above was introduced into HEK293T cells to obtain each transfectant, and SARS-CoV-2 NSP7, SARS-CoV-2 NSP8, N-terminal FLAG-labeled SARS-CoV-2 RdRp, and C-terminal FLAG-labeled SARS-CoV-2 RdRp expressed in each of the transfectant s obtained above were confirmed by Western blot analysis (FIG. 3a).

FIG. 3a is a diagram of Western blot analysis showing the result of analyzing the expression levels of SARS-CoV-2 NSP7, SARS-CoV-2 NSP8, N-terminal FLAG-labeled SARS-CoV-2 RdRp, or C-terminal FLAG-labeled SARS-CoV-2 RdRp expressed in HEK293T cells into which recombinant vector p-nsp7(SARS-CoV-2), p-nsp8(SARS-CoV-2), pN-termFlag-nsp12(SARS-CoV-2), or pC-termFlag-nsp12(SARS-CoV-2) was introduced.

As shown in FIG. 3a, it was confirmed that SARS-CoV-2 NSP7, SARS-CoV-2 NSP8, N-terminal FLAG-labeled SARS-CoV-2 RdRp, or C-terminal FLAG-labeled SARS-CoV-2 RdRp was expressed in each transfectant.

In particular, it was found that the expression level of N-terminal FLAG-labeled SARS-CoV-2 RdRp was relatively high compared to the expression level of C-terminal FLAG-labeled SARS-CoV-2 RdRp.

Accordingly, to compare the activity of N-terminal or C-terminal FLAG-labeled SARS-CoV-2 RdRp, (a) transfectant s in which p(+)FLuc-(-)UTR-NLuc reporter vector prepared in Example 1-1 and the recombinant vector pN-termFlag-nsp12 (SARS-CoV-2) prepared above were introduced into HEK293T cells; and (b) transfectant s in which p(+)FLuc-(-)UTR-NLuc reporter vector and pC-termFlag-nsp12(SARS-CoV-2) were into introduced into HEK293T cells were constructed, and the luminescence level was measured therefrom and compared (FIG. 3b). At this time, as a control, a transfectant in which the p(+)FLuc-(-)UTR-NLuc reporter vector was introduced into HEK293T cells alone was used.

FIG. 3b is a graph showing the result of comparing the NLuc activity derived from the N-terminal or C-terminal FLAG SARS-CoV-2 RdRp protein expressed in HEK293T cells into which recombinant vector pN-termFlag-nsp12 (SARS-CoV-2) or pC-termFlag-nsp12 (SARS-CoV-2) was introduced.

As shown in FIG. 3b, the relative NLuc activity was increased by the expression of N-terminal or FLAG-labeled SARS-CoV-2 RdRp, and the luciferase activity according to the FLAG-labeled position did not show a significant difference.

Example 1-3-2

Effect of nsp7 and nsp8 on SARS-CoV-2 RdRp Activity

It was confirmed whether NSP7 and NSP8 derived from SARS-CoV-2 could affect the SARS-CoV-2 RdRp activity expressed from the pN-termFlag-nsp12 (SARS-CoV-2).

Roughly, (a) transfectant s in which the p(+)FLuc-(-)UTR-NLuc reporter vector prepared in Example 1-1 and the recombinant vector pN-termFlag-nsp12(SARS-CoV-2) prepared above were introduced into HEK293T cells; and (b)

transfectant s in which p(+)FLuc-(-)UTR-NLuc reporter vector, pN-termFlag-nsp12(SARS-CoV-2), p-nsp7(SARS-CoV-2), and p-nsp8(SARS-CoV-2) were introduced into the HEK293T cells were constructed, and the luminescence level was measured from each transfectant and compared (FIG. 3c). At this time, as a control, a transfectant in which the p(+)FLuc-(-)UTR-NLuc reporter vector was introduced into HEK293T cells alone was used.

FIG. 3c is a graph showing the results of confirming whether SARS-CoV-2 NSP7 or SARS-CoV-2 NSP8 affects the activity of N-terminal FLAG-labeled SARS-CoV-2 RdRp.

As shown in FIG. 3c, it was confirmed that the luminescence level of the transfectant s in which SARS-CoV-2 NSP7 and SARS-CoV-2 NSP8 were expressed together with N-terminal FLAG-labeled SARS-CoV-2 RdRp showed a relatively high level compared to the luminescence level of the transfectant in which N-terminal FLAG-labeled SARS-CoV-2 RdRp was expressed alone.

Example 1-3-3

Optimization of Reporter Vector

After constructing p(+)FLuc-(-)UTR-NLuc with or without polyA33 of (-)3'-UTR, the relative NLuc activity according to the level of SARS-CoV-2 RdRp was compared by expressing various levels of SARS-CoV-2 RdRp together (FIG. 3d).

FIG. 3d a graph showing the result of comparing the NLuc/FLuc ratio derived from the N-terminal FLAG-labeled SARS-CoV-2 RdRp expressed in each HEK293T cell into which p(+)FLuc-(-)UTR-NLuc and pN-termFlag-nsp12(SARS-CoV-2) with polyA of (-)3'-UTR (w/A33) or without polyA (w/o A33) were introduced and various levels of SARS-CoV-2 RdRp were introduced.

As shown in FIG. 3d, it was confirmed that when the p(+)FLuc-(-)UTR-NLuc with or without polyA33 of (-)3'-UTR and pN-termFlag-nsp12 (SARS-CoV-2) were introduced into HEK293T cells, the relative NLuc activity was relatively increased when the p(+)FLuc-(-)UTR-NLuc without polyA33 of (-)3'-UTR was used compared to when the p(+)FLuc-(-)UTR-NLuc with polyA33 of (-)3'-UTR was used, and it was increased in a dose-dependent manner with respect to pN-termFlag-nsp12(SARS-CoV-2).

Therefore, it was found that SARS-CoV-2 3'-UTR does not require polyA sequence to translate the NLuc protein.

Example 2

Efficacy Evaluation of Cell-Based MERS-CoV RdRp Activity Reporter Assay System In order to confirm whether the cell-based MERS-CoV RdRp activity reporter assay system prepared in Example 1-2 shows a substantial effect, known ribavirin, sofosbuvir, favipiravir, lamivudine, zidovudine, valacyclovir, vidarabine, dasabuvir, and remdesivir were used to test the analysis system.

Roughly, HEK293T cells were inoculated into a 96-well plate and cultured overnight, then pN-termFlag-nsp12 vector and p(+)FLuc-(-)UTR-NLuc vector were added thereto and cultured for 24 hours to obtain transformed cells. The transformed cells were treated with the desired compound or 0.25% DMSO (control). The expression levels of FLuc and NLuc reporter genes expressed in these cells were measured using the Nano-Glo®Dual-Luciferase® Reporter Assay System (Promega Corporation). The relative activity of MERS-CoV RdRp was calculated through normalization using the ratio of NLuc activity to FLuc activity (NLuc/FLuc ratio). $IC_{50}$ (half-maximal inhibitory concentration), a concentration at which NLuc activity was reduced by 50% compared to the control group, was measured using non-linear regression analysis. The percent activity of Middle East respiratory syndrome Coronavirus (MERS-CoV) RNA dependent RNA polymerase (RdRp) at the maximum concentration of the test compound was determined using linear interpolation (Table 1).

[Table 1]

Percent activity of Middle East Respiratory Syndrome Coronavirus (MERS-CoV) RNA-dependent RNA Polymerase (RdRp) at Maximum Concentration of Test Compound

| Compound | Max dose (µM) | MERS-CoV RdRp activity (%) |
|---|---|---|
| ribavirin | 100 | 60.3 ± 2.9 |
| sofosbuvir | 100 | 62.4 ± 5.3 |
| favipiravir | 100 | 85.8 ± 2.4 |
| lamivudine | 100 | 98.3 ± 1.2 |
| zidovudine | 100 | 110.8 ± 3.7 |
| vidarabine | 100 | 89.9 ± 2.9 |
| valacyclovir | 100 | 90.2 ± 3.2 |
| dasabuvir | 10 | 51.5 ± 4.2 |
| remdesivir | 12 | 22.3 ± 0.3 |

Example 2-1

Evaluation Using Ribavirin

Ribavirin is a guanosine analog and a broad-spectrum antiviral agent that has been approved to treat RSV, HCV, Crimean-Congo hemorrhagic fever virus, Lassa virus, and Hantavirus infections based on its ability to prevent viral RNA synthesis.

Ribavirin is known to inhibit MERS-CoV infection in vitro with $IC_{50}$ values of 41.45 µg/mL and 13.26 µg/mL, respectively, in Vero RML6 and LLC-MK2 cells.

The assay system was treated with ribavirin at various concentrations (0 µM, 3.13 µM, 6.25 µM, 12.5 µM, 25 µM, 50 µM, or 100 µM), and its efficacy was evaluated (FIG. 4a and Table 1).

FIG. 4a is a graph showing the evaluation results using various concentrations of ribavirin in the cell-based MERS-CoV RdRp activity reporter assay system.

As shown in FIG. 4a and Table 1, it was confirmed that 100 µM ribavirin inhibited the activity of MERS-CoV RdRp by about 40%.

Example 2-2

Evaluation Using Sofosbuvir

Sofosbuvir is a clinically approved uridine nucleotide known to block the HCV NS5B protein, also known as RdRp.

The assay system was treated with sofosbuvir at various concentrations (0 µM, 3.13 µM, 6.25 µM, 12.5 µM, 25 µM, 50 µM, or 100 µM and its efficacy was evaluated (FIG. 4b and Table 1).

FIG. 4b is a graph showing the evaluation results using various concentrations of sofosbuvir in the cell-based MERS-CoV RdRp activity reporter assay system.

As shown in FIG. 4b and Table 1, it was confirmed that 100 µM sofosbuvir inhibited MERS-CoV RdRp activity by about 40%.

Example 2-3

Evaluation Using Favipiravir

Favipiravir (T-705) acts as a purine analog and is known to inhibit influenza virus polymerase by inducing lethal RNA transfer mutations.

The assay system was treated with various concentrations (0 µM, 3.13 µM, 6.25 µM, 12.5 µM, 25 µM, 50 µM, or 100 µM) of favipiravir, and its efficacy was evaluated (FIG. 4c and Table 1).

FIG. 4c is a graph showing the evaluation results using various concentrations of favipiravir in the cell-based MERS-CoV RdRp activity reporter assay system.

As shown in FIG. 4c and Table 1, although favipiravir is known to inhibit the activity of RdRp protein in various RNA viruses, it was confirmed that MERS-CoV RdRp activity was reduced by about 10% when favipiravir was treated at a concentration of 100 µM.

Example 2-4

Evaluation Using Lamivudine

Lamivudine is known as a nucleoside analog that acts as a reverse transcriptase inhibitor and is known to be used for the inhibition of HIV infection.

The assay system was treated with various concentrations (0 µM, 3.13 µM, 6.25 µM, 12.5 µM, 25 µM, 50 µM, or 100 µM) of lamivudine, and its efficacy was evaluated (FIG. 4d and Table 1).

FIG. 4d is a graph showing the evaluation results using various concentrations of lamivudine in the cell-based MERS-CoV RdRp activity reporter assay system.

As shown in FIG. 4d and Table 1, it was confirmed that lamivudine at the maximum concentration of 100 µM did not reduce the MERS-CoV RdRp activity.

Example 2-5

Evaluation Using Zidovudine

Zidovudine is known as a nucleoside analog that acts as a reverse transcriptase inhibitor, and is known to be used for the inhibition of HIV infection.

The assay system was treated with zidovudine at various concentrations (0 µM, 3.13 µM, 6.25 µM, 12.5 µM, 25 µM, 50 µM, or 100 µM), and its efficacy was evaluated (FIG. 4e and Table 1).

FIG. 4e is a graph showing the evaluation results using various concentrations of zidovudine in the cell-based MERS-CoV RdRp activity reporter assay system.

As shown in FIG. 4e and Table 1, it was confirmed that zidovudine at the maximum concentration of 100 µM did not reduce the MERS-CoV RdRp activity.

Example 2-6

Evaluation Using Valacyclovir

Valacyclovir is a nucleoside analog that inhibits HSV infection by acting as a DNA polymerase inhibitor.

The assay system was treated with valacyclovir at various concentrations (0 μM, 3.13 μM, 6.25 μM, 12.5 μM, 25 μM, 50 μM, or 100 μM), and its efficacy was evaluated (FIG. 4*f* and Table 1).

FIG. 4*f* is a graph showing the evaluation results using various concentrations of valacyclovir in the cell-based MERS-CoV RdRp activity reporter assay system.

As shown in FIG. 4*f* and Table 1, it was confirmed that valacyclovir at the maximum concentration of 100 μM did not reduce the MERS-CoV RdRp activity.

Example 2-7

Evaluation Using Vidarabine

Vidarabine is a nucleoside analog that inhibits HSV infection by acting as a viral DNA polymerase inhibitor.

The assay system was treated with vidarabine at various concentrations (0 μM, 3.13 μM, 6.25 μM, 12.5 μM, 25 μM, 50 μM, or 100 μM), and its efficacy was evaluated (FIG. 4*g* and Table 1).

FIG. 4*g* is a graph showing the evaluation results using various concentrations of vidarabine in the cell-based MERS-CoV RdRp activity reporter assay system.

As shown in FIG. 4*g* and Table 1, it was confirmed vidarabine at the maximum concentration of 100 μM did not reduce the MERS-CoV RdRp activity.

In addition, although it did not show cytotoxicity, it was confirmed that FLuc and NLuc activities were unexpectedly reduced in a concentration-dependent manner.

These results were attributed to the fact that vidarabine inhibited the transcription/translation process of host cells, but did not affect the NLuc/FLuc ratio or MERS-CoV RdRp activity.

Example 2-8

Evaluation Using Dasabuvir

Dasabuvir is a derivative of benzothiadiazine that acts as a non-nucleoside inhibitor of HCV NSSB by reacting with a conserved amino acid located near the active region of the HCV NSSB palm domain (FIG. 5*a*).

FIG. 5*a* is a schematic diagram showing the chemical structure of dasabuvir. First, in order to analyze the cytotoxicity of dasabuvir, HEK293T cells were inoculated into a 96-well plate and cultured overnight, then various concentrations of dasabuvir were added and cultured for 18 hours. Toxicity of the cells was analyzed using CellTiter 96® AQueous One Solution Cell Proliferation Assay (Promega Corporation), and absorbance was measured at a wavelength of 490 nm using GloMax® Discover Microplate Reader (Promega Corporation) (FIG. 5*b*).

FIG. 5*b* is a graph showing the results of comparing the cell viability of HEK293T cells treated with various concentrations of dasabuvir.

As shown in FIG. 5*b*, when the cells were treated with 10 μM dasabuvir, no cytotoxicity was observed, but when the cells were treated at a concentration exceeding 10 μM, cytotoxicity was observed, and it was confirmed that the concentration at which cytotoxicity was reduced by half in HEK293T cells was 27.143 μM.

Next, the assay system was treated with various concentrations (0 μM, 0.625 μM, 1.25 μM, 2.5 μM, 5 μM, 10 μM, or 20 μM) of dasabuvir, and its efficacy was evaluated (FIG. 5C and Table 1).

FIG. 5*c* is a graph showing the evaluation results using various concentrations of dasabuvir in the cell-based MERS-CoV RdRp activity reporter assay system.

As shown in FIG. 5*c* and Table 1, it was confirmed that 10 μM dasabuvir reduced MERS-CoV RdRp activity by about 50%.

Finally, a non-linear regression analysis was performed based on the evaluation results using various concentrations of dasabuvir in the cell-based MERS-CoV RdRp activity reporter assay system (FIG. 5*d*).

FIG. 5*d* is a graph showing the results of performing non-linear regression analysis on the results of dasabuvir used in the cell-based MERS-CoV RdRp activity reporter assay system.

As shown in FIG. 5*d*, it was confirmed that the $IC_{50}$ value of dasabuvir was 11.606 μM.

From the above results, it can be seen that, when using dasabuvir, MERS-CoV RdRp activity can be significantly inhibited, but not completely inhibited.

Example 2-9

Evaluation Using Remdesivir

Remdesivir is a monophosphoramidate prodrug of an adenosine analog. It inhibits MERS-CoV infection with an $IC_{50}$ value of 0.074±0.023 μM in vitro using human airway epithelial cells, and it is known that remdesivir targets RdRp and exoribonucleases (nsp14, ExoN) in MHV through resistance mutation studies (FIG. 6*a*).

FIG. 6*a* is a schematic diagram showing the chemical structure of remdesivir.

First, the cytotoxicity of remdesivir was analyzed by the method of Examples 2-8 (FIG. 6*b*).

FIG. 6*b* is a graph showing the results of comparing the cell viability of HEK293T cells treated with various concentrations of remdesivir.

As shown in FIG. 6*b*, it was confirmed that no cytotoxicity was observed even when treated with 12 μM remdesivir.

Next, the assay system was treated with various concentrations (0 μM, 0.56 μM, 0.93 μM, 1.56 μM, 2.59 μM, 4.32 μM, 7.20 μM, or 12.00 μM) of remdesivir, and its efficacy was evaluated (FIG. 6*c* and Table 1).

FIG. 6*c* is a graph showing the evaluation results using various concentrations of remdesivir in a cell-based MERS-CoV RdRp activity reporter assay system.

As shown in FIG. 6*c* and Table 1, it was confirmed that when remdesivir was treated at 12 μM, the FLuc activity was not reduced, but the NLuc activity was reduced in a dose-dependent manner.

Finally, a non-linear regression analysis was performed based on the evaluation results using various concentrations of remdesivir in the cell-based MERS-CoV RdRp activity reporter assay system (FIG. 6*d*).

FIG. 6*d* is a graph showing the results of performing non-linear regression analysis on the results of remdesivir used in the cell-based MERS-CoV RdRp activity reporter assay system.

As shown in FIG. 6*d*, it was confirmed that the $IC_{50}$ value of remdesivir was 5.028±0.035 μM.

From the above results, it was found that most of the MERS-CoV RdRp activity could be inhibited when remdesivir was used.

Example 3

Efficacy Evaluation of Cell-Based SARS-CoV-2 RdRp Activity Reporter Assay System In order to confirm whether the cell-based SARS-CoV-2 RdRp activity reporter assay system prepared in Example 1-3 shows a substantial effect, the assay system was tested using remdesivir evaluated in Example 2.

Roughly, HEK293T cells were inoculated into a 96-well plate and cultured overnight, then pN-termFlag-nsp12 (SARS-CoV-2) vector and p(+)FLuc-(–)UTR-NLuc vector were added thereto and cultured for 24 hours to obtain transformed cells. The transformed cells were treated with remdesivir at various concentrations (0.78 μM, 1.17 μM, 1.76 μM, 2.63 μM, 3.95 μM, and 5.93 μM) or 0.25% DMSO (Mock). The expression levels of FLuc and NLuc reporter genes expressed in these cells were measured using a Nano-Glo®Dual-Luciferase® Reporter Assay System (Promega Corporation). The relative activity of MERS-CoV RdRp was calculated through normalization using the ratio of NLuc activity to FLuc activity (NLuc/FLuc ratio). $IC_{50}$ (half-maximal inhibitory concentration), a concentration at which NLuc activity was reduced by 50% compared to the control group, was measured using non-linear regression analysis (FIGS. 7a and 7b).

FIG. 7a is a graph showing the evaluation results using various concentrations of remdesivir in a cell-based SARS-CoV-2 RdRp activity reporter assay system.

As shown in FIG. 7a, it was confirmed that when remdesivir was treated at 5.93 μM, the FLuc activity was not reduced, but the NLuc activity was reduced in a dose-dependent manner.

In addition, a non-linear regression analysis was performed based on the evaluation results using various concentrations of remdesivir in the cell-based SARS-CoV-2 RdRp activity reporter assay system (FIG. 7b).

FIG. 7b is a graph showing the results of performing non-linear regression analysis on the results of remdesivir used in the cell-based SARS-CoV-2 RdRp activity reporter assay system.

As shown in FIG. 7b, it was confirmed that the $IC_{50}$ value of remdesivir was 3.482 μM.

From the above results, it was found that most of the SARS-CoV-2 RdRp activity could be inhibited when remdesivir was used.

Example 4

Validation of Reliability and Reproducibility of Cell-Based MERS-CoV RdRp Activity Reporter Assay System in HTS The Z-factor is the most widely used parameter for evaluation and validation of HTS systems.

In the present invention, in order to evaluate the discrimination ability of the assay for MERS-CoV RdRp activity, the Z-factor was calculated using the relative NLuc activity obtained from the negative control and the positive control.

In addition, the Z'-factor was calculated using data obtained from the positive control and experimental group to evaluate the availability of remdesivir as a positive control related to MERS-CoV RdRp inhibition.

Roughly, the following negative control group, positive control group and experimental group were established:

1) Negative control (n=40 wells) treated with 0.025% DMSO after double transfection of p(+)FLuc-(–)UTR-NLuc and pcDNA3.1 (empty vector);

2) Positive control (n=40 wells) treated with 0.025% DMSO after double transfection of p(+)FLuc-(–)UTR-NLuc and pN-termFlag-nsp12;

3) Experimental group (n=40 wells) treated with 12 μM remdesivir after double transfection of p(+)FLuc-(–) UTR-NLuc and pN-termFlag-nsp12.

Z-factor and Z'-factor values were calculated by substituting the values measured in the established negative control group, positive control group, and experimental group into the formulae below (FIG. 8).

$$Z\text{-factor}=1-[(3SD_{Negative}+3SD_{Positive})/|\text{mean}_{Negative}+\text{mean}_{Positive}|].$$

$$Z'\text{-factor}=1-[(3SD_{Inhibitor}+3SD_{Positive})/|\text{mean}_{Inhibitor}-\text{mean}_{Positive}|].$$

For both formulae, the standard deviation and mean values of each group represent the relative NLuc activity obtained from each group.

FIG. 8 is a graph showing the analysis results using Z-factor and Z'-factor values of the screening composition for a therapeutic agent for Middle East respiratory syndrome provided by the present invention.

As shown in FIG. 8, the Z-factor and Z'-factor values demonstrating that the cell-based MERS-CoV RdRp activity reporter assay system in the HTS system can reliably and reproducibly identify MERS-CoV RdRp inhibitors were 0.778 and 0.782, respectively.

From the foregoing, a skilled person in the art to which the present invention pertains will be able to understand that the present application may be embodied in other specific forms without modifying the technical concepts or essential characteristics of the present invention. In this regard, the described embodiments are to be considered in all respects only as illustrative and not restrictive. The scope of the present invention is therefore indicated by the appended claims rather than by the foregoing description. All changes which come within the meaning and range of equivalency of the claims are to be embraced within the scope of the present invention.

The invention claimed is:

1. A screening composition for a therapeutic agent for coronavirus infection, comprising:
    (a) a CoV RdRp expression vector comprising a FLAG-labeled CoV (coronavirus) nsp12 gene at the N-terminus; and
    (b) a bicistronic reporter vector comprising: a firefly luciferase gene in the sense direction ((+)FLuc) and a NanoLuc luciferase gene in the antisense direction ((−)NLuc); wherein the (−)NLuc forms domains (3'-UTR, NLuc and 5'-UTR) interposed between 3'-UTR and 5'-UTR in the antisense direction derived from CoV; wherein the 3'-UTR, NLuc, and 5'-UTR domains in the antisense direction are in the form in which a ribozyme self-cleaving sequence derived from hepatitis delta virus (HDV) is bound to each of the 5'- and 3'-ends thereof; and a firefly luciferase gene in the sense direction independently of the domain in the antisense direction.

2. The composition of claim 1, wherein the CoV nsp12 gene is a MERS-CoV nsp12 gene or a SARS-CoV-2 nsp12 gene.

3. The composition of claim 2, wherein the MERS-CoV nsp12 gene comprises a nucleotide sequence of SEQ ID NO: 1.

4. The composition of claim 2, wherein the SARS-CoV-2 nsp12 gene comprises a nucleotide sequence of SEQ ID NO: 2.

5. The composition of claim 1, wherein the CoV RdRp expression vector is a MERS-CoV RdRp expression vector comprising the MERS-CoV nsp12 gene.

6. The composition of claim 1, wherein the CoV RdRp expression vector is a SARS-CoV-2 RdRp expression vector comprising the SARS-CoV-2 nsp12 gene.

7. The composition of claim 1, wherein the CoV RdRp expression vector further comprises a gene selected from the group consisting of a CoV nsp7 gene, CoV nsp8 gene, and a combination thereof.

8. The composition of claim 7, wherein the CoV nsp7 gene is a MERS-CoV nsp7 gene or a SARS-CoV-2 nsp7 gene.

9. The composition of claim 8, wherein the MERS-CoV nsp7 gene comprises a nucleotide sequence of SEQ ID NO: 3.

10. The composition of claim 8, wherein the SARS-CoV-2 nsp7 gene comprises a nucleotide sequence of SEQ ID NO: 4.

11. The composition of claim 7, wherein the CoV nsp8 gene is a MERS-CoV nsp8 gene or a SARS-CoV-2 nsp8 gene.

12. The composition of claim 11, wherein the MERS-CoV nsp8 gene comprises a nucleotide sequence of SEQ ID NO: 5.

13. The composition of claim 11, wherein the SARS-CoV-2 nsp8 gene comprises a nucleotide sequence of SEQ ID NO: 6.

14. The composition of claim 1, wherein the firefly luciferase gene comprises a nucleotide sequence of SEQ ID NO: 7.

15. The composition of claim 1, wherein the NanoLuc luciferase gene comprises a nucleotide sequence of SEQ ID NO: 8.

16. The composition of claim 1, wherein the composition is in the form in which each of the CoV RdRp expression vector and the reporter vector are separately included.

17. The composition of claim 1, wherein the composition is in the form containing a transfectant, into which the CoV RdRp expression vector and the reporter vector are introduced.

18. The composition of claim 1, wherein the coronavirus infection is Middle East respiratory syndrome or Coronavirus disease-19 (COVID-19).

19. A screening kit for a therapeutic agent for coronavirus, comprising the screening composition for a therapeutic agent for coronavirus of any one of claims 1 and 2 to 18.

20. A method for screening a therapeutic agent for coronavirus infection, comprising:
    (a) preparing a transfectant into which a CoV RdRp expression vector and a reporter vector included in the screening composition for a therapeutic agent for coronavirus infection according to any one of claims 1 and 2 to 18 are introduced together;
    (b) treating the prepared transfectant with a candidate material expected to inhibit the activity of coronavirus-derived RNA-dependent RNA polymerase (CoV RdRp); and
    (c) measuring the fluorescence level derived from Nano-Luc luciferase after treating the candidate material.

21. The method of claim 20, wherein in step (b), the method further comprises pre-measuring the fluorescence level derived from NanoLuc luciferase in the transfectant before treating the candidate material.

22. The method of claim 20, wherein in step (c), the method distinguished the candidate as an inhibitor of CoV RdRp activity when the fluorescence level derived from NanoLuc luciferase is reduced.

* * * * *